(12) United States Patent
Thompson et al.

(10) Patent No.: US 6,203,787 B1
(45) Date of Patent: Mar. 20, 2001

(54) TREATING TUMORS USING IMPLANTS COMPRISING COMBINATIONS OF ALLOGENEIC CELLS

(75) Inventors: James A. Thompson, Alliso Viejo; Gale A. Granger, Laguna Beach, both of CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/169,561

(22) Filed: Oct. 9, 1998

Related U.S. Application Data
(60) Provisional application No. 60/061,766, filed on Oct. 10, 1997, now abandoned.

(51) Int. Cl.[7] .............................. A01N 63/00; C12N 5/06; C12N 5/08

(52) U.S. Cl. .................... 424/93.3; 424/93.7; 424/93.71; 435/325; 435/347; 435/366; 435/372; 435/373; 435/383

(58) Field of Search ................................ 424/93.3, 93.7, 424/93.71; 435/373, 325, 347, 366, 372, 383

(56) References Cited

U.S. PATENT DOCUMENTS

| | | | |
|---|---|---|---|
| 5,192,537 | 3/1993 | Osband | 424/85.2 |
| 5,308,626 | 5/1994 | Landucci et al. | 424/93 |
| 5,476,993 | 12/1995 | Richmond | 588/252 |
| 5,484,596 | 1/1996 | Hanna, Jr. et al. | 424/277.1 |
| 5,602,305 | 2/1997 | Pober et al. | 800/2 |
| 5,663,481 | 9/1997 | Gallinger et al. | 800/2 |
| 5,837,233 | 11/1998 | Granger | 424/93.1 |

FOREIGN PATENT DOCUMENTS

| | | |
|---|---|---|
| 379 554 B1 | 5/1996 | (EP) . |
| WO 91/01760 | 2/1991 | (WO) . |
| WO 96/07433 | 3/1996 | (WO) . |
| WO 96/29394 | 9/1996 | (WO) . |
| WO 98/16238 | 4/1998 | (WO) . |

OTHER PUBLICATIONS

Gastl et al., "Retroviral Vector–mediated by Lymphokine Gene Transfer Into Human Renal Cancer Cells," *Cancer Research* 52:6229–6236 (1992).

Kondo et al., "Rationale for a Novel Immunotherapy of Cancer with Allogeneic Lymphocyte Infusion," *Medical Hypotheses* 15:241–277 (1984).

Kruse et al., "Analysis of Interleukin 2 and Various Effector Cell Populations in Adoptive Immunotherapy of 9L Rat Gliosarcoma: Allogeneic Cytotoxic T Lymphocytes Prevent Tumor Take," *Proc. Natl. Acad. Sci. USA* 87:9577–9581 (1990).

Kruse et al., "Intracranial Administration of Single of Multiple Source Allogeneic Cytotoxic T Lymphocytes: Chronic Therapy for Primary Brain Tumors," *J. Neurooncol.* 19:161–168 (1994).

Kruse et al., "Immune Therapy of Recurrent Malignant Gliomas: Intracavitary Allogeneic Cytotoxic T Lymphocytes and Human Recombinant Interleukin–2," *FASEB J.* 10 (6) :A2387 (1996).

Kruse et al., "Development of Human Allogenic CTL in an Artificial Capillary System for Intracavitary Treatment of Malignant Glioma," *Proc. Am. Assoc. Cancer Res.* 36:474 (1995).

Leshem et al., "In vitro elicitation of cytotoxic response against a nonimmunogenic murine tumor by allosensitization," *Cancer Immunology Immunotheraphy* 17:117–123 (1984).

Merchant et al., "Adoptive Immunotherapy for Recurrent Glioblastoma Multiforem Using Lymphokine Activated Killer Cells and Recombinant Interleukin–2," *Cancer* 62:665–671 (1988).

Merchant et al., "Immunotherapy for Malignant Glioma Using Human Recombinant Interleukin–2 and Activated Autologous Lymphocytes. A Review of Pre–clinical and Clinical Investigation," *J. Neurooncol.* 8:173–188 (1990).

Pardoll, "New Strategies for Active Immunotherapy with Genetically Engineered Tumor Cells," *Current Opinion in Immunology* 4:619–623 (1992).

Redd et al., "Allogeneic Tumor–specific Cytotoxic T Lymphocytes," *Cancer Immunol. Immunother.* 34:349–354 (1992).

Rosenberg et al., "A Progress Report on the Treatment of 157 Patients with Advanced Cancer Using Lymphokine–activated Killer Cells and Interleukin–2 or high–dose inerleuki–2 alone," *New England Journal of Medicine* 316:889–897 (1987).

Rosenberg et al., "Gene Transfer into Humans—Immunotherapy of Patients with Advanced Melanoma, Using Tumor–infiltrating Lymphocytes Modified by Retroviral Gene Transduction," *New England Journal of Medicine* 323:570–578 (1990).

Saito et al., "Immunotherapy of Bladder Cancer with Cytokine Gene–Modified Tumor Vaccines," *Cancer Research* 54:3516–3520 (1994).

(List continued on next page.)

*Primary Examiner*—Geetha P. Bansal
(74) *Attorney, Agent, or Firm*—Carol L. Francis; Bozicevic, Field & Francis, LLP

(57) ABSTRACT

This invention provides methods and compositions for treating tumors by implanting near the tumor an alloactivated cell population. The cell population is made up of a plurality of third-party donor cells that have been cultured together ex vivo, and harvested near the time of peak cytokine secretion. Once placed in the tumor bed, the alloactivated cells recruit active participation of the host, which then reacts against the tumor and provides a level of ongoing protection. Employing multiple third party donor cells confers particular advantages in terms of effectiveness, timing, and ease of use.

18 Claims, 7 Drawing Sheets

OTHER PUBLICATIONS

Schirrmacher et al., "Workshop: Active Specific Immunotherapy with Tumor Cell Vaccines," *J. Cancer Res. Clin. Oncol.* 121:487–489 (1995).

Strausser et al., "Lysis of Human Solid Tumors by Autologous Cells Sensitized In Vitro to Alloantigens," *J. Immunol.* 127:266–271 (1981).

Vieweg et al., "Immunotherapy of Prostate Cancer in the Dunning Rat Model: Use of Cytokine Gene Modified Tumor Vaccines," *Cancer Res.* 54:1760–1765 (1994).

Zarling et al., "Generation of Cytotoxic T Lymphocytes to Autologous Human Leukaemia Cells by Sensitisation to Pooled Allogeneic Norman Cells," *Nature* 274:269–271 (1978).-

TREATING TUMORS USING IMPLANTS COMPRISING COMBINATIONS OF ALLOGENEIC CELLS

REFERENCE TO RELATED APPLICATION

This application claims the priority benefit of U.S. provisional application Ser. No. 60/061,766, filed Oct. 10, 1997 ABN. The priority application is hereby incorporated herein by reference in its entirety.

FIELD OF THE INVENTION

The present invention relates generally to the fields of cellular immunology and cancer therapy. More specifically, it relates to the treatment of tumors or the generation of an anti-tumor immune response by implanting a mixture of alloactivated allogeneic cells in or around the tumor site.

BACKGROUND

Cancer continues to be a leading cause of mortality around the globe. Traditional regimens of cancer management have been successful in the management of a selective group of circulating and slow-growing solid cancers. However, many solid tumors are resistant to traditional approaches, and the prognosis in such cases is correspondingly grave.

One example is brain cancer. Each year, approximately 15,000 cases of high grade astrocytomas are diagnosed in the United States. The number is growing in both pediatric and adult populations. Standard treatments include cytoreductive surgery followed by radiation therapy or chemotherapy. There is no cure, and virtually all patients ultimately succumb to recurrent or progressive disease. The overall survival for grade IV astrocytomas (glioblastoma multiforme) is poor, with ~50% of patients dying in the first year after diagnosis. Because these tumors are aggressive and highly resistant to standard treatments, new therapies are needed.

Another example is pancreatic cancer, the fifth leading cause of cancer-related deaths in the United States. The disease is associated with a high mortality rate, with a medium survival for untreated patients after diagnosis of about 4 months. Ninety percent of pancreatic cancer patients initially present with locally advanced, surgically unresectable disease. Current therapy for these patients is strictly palliative and does not significantly impact on overall patient survival. Most recently, the chemotherapeutic agent, Gemcitabine (GEMZAR™) was shown to improve overall median survival to 5.7 months compared to that of 5-fluorouracyl (4.2 months) and had a better clinical benefit index. However, it is clear that even with these newer agents, palliation of the disease is highly temporary.

An emerging area of cancer treatment is immunotherapy. There are a number of immunological strategies under development, including: 1. Adoptive immunotherapy using stimulated autologous cells of various kinds; 2. Systemic transfer of allogeneic lymphocytes; 3. Vaccination at a distant site to generate a systemic tumor-specific immune response; 4. Implantation of immune cells directly into the tumor.

The first of these strategies, adoptive immunotherapy, is directed towards providing the patient with a level of enhanced immunity by stimulating cells ex vivo, and then readministering them to the patient. The cells are histocompatible with the subject, and are generally obtained from a previous autologous donation.

One version is to stimulate autologous lymphocytes ex vivo with tumor-associated antigen to make them tumor-specific. Zarling et al. (1978) *Nature* 274:269–71 generated cytotoxic lymphocytes in vitro against autologous human leukemia cells. In U.S. Pat. No. 5,192,537, Osband suggests activating a tumor patient's mononuclear cells by culturing them ex vivo in the presence of tumor cell extract and a non-specific activator like phytohemagglutinin or IL-1, and then treating the culture to deplete suppresser cell activity. Despite these experimental observations, systemic administration of ex vivo-stimulated autologous tumor-specific lymphocytes has not become part of standard cancer therapy.

Autologous lymphocytes and killer cells may also be stimulated non-specifically. In one example, Fc receptor expressing leukocytes that can mediate an antibody-dependent cell-mediated cytotoxicity reaction are generated by culturing with a combination of IL-2 and IFN-γ (U.S. Pat. No. 5,308,626). In another example, peripheral blood-derived lymphocytes cultured in IL-2 form lymphokine-activated killer (LAK) cells, which are cytolytic towards a wide range of neoplastic cells, but not normal cells. In combination with high dose IL-2, LAK cells have had some success in the treatment of metastatic human melanoma and renal cell carcinoma. Rosenberg (1987) *New Engl. J Med.* 316:889–897. For examples of trials conducted using LAK in the treatment of brain tumors, see Merchant et al. (1988) *Cancer* 62:665–671 & (1990) *J. Neuro-Oncol.* 8:173–198. While not associated with serious clinical complications, efficacy is typically only anecdotal or transient.

Another form of adoptive therapy using autologous cells has been proposed based on observations with tumor-infiltrating lymphocytes (TIL). TILs are obtained by collecting lymphocyte populations infiltrating into tumors, and culturing them ex vivo with IL-2. TILs have activity and tumor specificity superior to LAK cells, and have been experimentally administered, for example, to humans with advanced melanoma. Rosenberg et al. (1990) *New Engl. J. Med.* 323:570–578. Unfortunately, TILs can only be prepared in sufficient quantity to be clinically relevant in a limited number of tumor types, and remain experimental.

The second of the strategies for cancer immunotherapy listed earlier is adoptive transfer of allogeneic lymphocytes. The rationale of this experimental strategy is to create a general level of immune stimulation, and thereby overcome the anergy that prevents the host's immune system from rejecting the tumor. Strausser et al. (1981) *J. Immunol.* Vol. 127, No. 1 describe the lysis of human solid tumors by autologous cells sensitized in vitro to alloantigens. Zarling et al. (1978) *Nature* 274:269–71 demonstrated human anti-lymphoma responses in vivo following sensitization with allogeneic leukocytes. Kondo et al. (1984) *Med Hypotheses* 15:241–77 observed objective responses of this strategy in 20–30% of patients, and attributed the effect to depletion of suppressor T cells. The studies were performed on patients with disseminated or circulating disease. Even though these initial experiments were conducted over a decade ago, the strategy has not gained general acceptance, especially for the treatment of solid tumors.

The third of the immunotherapy strategies listed earlier is the generation of an active systemic tumor-specific immune response of host origin by administering a vaccine composition at a site distant from the tumor.

Various types of vaccines have been proposed, including isolated tumor-antigen vaccines and anti-idiotype vaccines. Another approach is to use tumor cells from the subject to be treated, or a derivative of such cells. For review see, Schirrmacher et al. (1995) *J Cancer Res. Clin. Oncol.* 121:487–489. In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

In yet another approach, autologous or syngeneic tumor cells are genetically altered to produce a costimulatory molecule. For reviews see, Pardoll et al. (1992) *Curr. Opin. Immunol.* 4:619–23; Saito et al. (1994) *Cancer Res.* 54:3516–3520; Vieweg et al.(1994) *Cancer Res.* 54:1760–1765; Gastl et al. (1992) *Cancer Res.* 52:6229–6236; and WO 96/07433. Tumor cells have been genetically altered to produce TNF-α, IL-1, IL-2, IL-3, IL-4, IL-6, IL-7, IL-10, IFN-α, IFN-γ and GM-CSF.

International patent application WO 98/16238 describes cancer immunotherapy using autologous tumor cells combined with allogeneic cytokine-secreting cells. The vaccines comprise a source of tumor-associated antigen, particularly tumor cells from the patient to be treated, combined with an allogeneic cytokine-secreting cell line. Exemplary cytokines are IL-4, GM-CSF, IL-2, TNF-α, and M-CSF in the secreted or membrane-bound form. The cytokine-producing cells provide immunostimulation in trans to generate a specific immune response against the tumor antigen. Vaccines can be tailored for each type of cancer or for each subject by mixing tumor antigen with an appropriate number of cytokine-producing cells, or with a cocktail of such cells producing a plurality of cytokines at a favorable ratio.

The fourth of the immunotherapy strategies listed earlier is intra-tumor implantation, directed at delivering effector cells directly to the site of action. The proximity of the effector cells to the target is supposed to promote the ability of the transplanted cells to react with the tumor, generating a graft versus tumor response.

Kruse et al. (*Proc. Natl. Acad. Sci USA*, 87:9377–9381, 1990) analyzed various effector cell populations in adoptive immunotherapy of the 9L rat gliosarcoma cell line. Different cell populations were prepared that were designed to have a direct effector function against the cancer cells. Included were syngeneic lymphocytes, nonadherent lymphocyte-activated killer (LAK) cells, adherent LAK cells, syngeneic cytotoxic T lymphocytes (CTL) raised against tumor antigens, and allogeneic CTL raised against alloantigens. The allogeneic cytotoxic T lymphocytes were claimed to prevent tumor take. The CTL were prepared by coculturing thoracic duct lymphocytes from one inbred rat strain with spleen cells from rats syngeneic to the challenged animals, under conditions and for a period designed to enrich for cytotoxic effector cells. Treatment was effected by coinjecting the CTL with the tumor cells into the brains of rats in conjunction with recombinant IL-2, and then readministering the CTL on two subsequent occasions. The regimen was claimed to forestall tumor take by 17 days. The authors state that the tumor is successful in the brain, because the brain is an immunologically privileged site which prevents the administered cells from being eliminated before they perform their function. A corollary of this is that the treatment would not be effective at other sites (such as the pancreas and the breast) that are not immunologically privileged.

In a subsequent study, Kruse et al. (*J. Neuro-Oncol.*, 19:161–168, 1994) performed intracranial administrations of single or multiple source allogeneic cytotoxic T lymphocytes. In this study, the 9L cancer cell line was injected into rats only 6 days before the initiation of treatment. A series of four injections of allogeneic T lymphocytes within the next 17 days was performed, and had the effect of extending the median life span of the rats by 19 days (about the same interval as the treatment protocol). There is no evidence for any lasting effect, despite the fact that four doses of the effector cells are given. This is consistent with the author's hypothesis that the tumoricidal effect is generated by the CTL themselves, and disappears once the administered cells are eliminated.

Two other publications by the same group demonstrates the natural progression of this CTL implantation technology in a direction towards greater enrichment for cells with a direct effector action against the tumor.

J. M. Redd, et al. *Cancer Immunol. Immunother.*, 34:349, 1992 describe a method of generating allogeneic tumor-specific cytotoxic T lymphocytes. CTL were generated in culture from an inbred rat strain allogeneic to the tumor cell line. The cells were found to lyse both tumor cells and Con A stimulated lymphoblasts of the same tissue type. The tumor-specific subset was deliberately selected and enriched as being specific for a determinant expressed only by the tumor. The article concludes by stating that the ultimate goal of the authors is to transfer the technology to humans using allogeneic CTL lacking specificity for normal brain antigens (i.e., depleted of alloreactive cells). This is a significant elucidation of the previous article by Kruse et al. in *Proc. Natl. Acad. Sci.* (supra, p. 9579 col. 1), in which they refer to two types of allogeneic CTL, one of which is tumor specific and one of which is allospecific. The yield of tumor specific cells was substantially lower. The article by Redd et al. teaches that the tumor specific cells are preferred, and provides a way of enriching for them when using cultured rat cells.

More recently, Kruse et al. (*Proc. Am. Assoc. Cancer Res.* 36:474, 1995; FASEB J. 10:A1413, 1996) briefly outline a clinical study of human brain cancer patients. The patient's lymphocytes were expanded with OKT3 and IL-2, then co-cultured with allogeneic donor cells for 18–21 days in the presence of IL-2. Such culture conditions would result in a population highly enriched for terminally differentiated effector cells. Patients enrolled in the Phase I study received CTL into the tumor bed and were placed with a catheter for subsequent infusions. Ongoing treatment involved 1 to 5 treatment cycles every other month, with each cycle consisting of 2–3 CTL infusates within a 1 to 2 week period. Again, the ongoing necessity to readminister the cells is consistent with the author's stated objective of providing cells with a direct cytolytic effect on the tumor.

The necessity of ongoing repeated administration of the effector cells to the tumor through a cannula severely limits the practical utility of this technology, both in terms of expense and the inconvenience to the patient.

In view of the limitations of may of these strategies, new approaches to the treatment of cancer are needed.

Considerable progress was made towards a simpler and more effective immunotherapeutic strategy by the development of cytoimplants. See International patent application WO 96/29394, a "Method for Treating Tumors". Potent cellular compositions are placed directly into the tumor bed, leading to beneficial effects for patients with different types of cancers. The method can be conducted as follows: The tumor patient's leukocytes are co-cultured in a mixed lymphocyte cell reaction with healthy lymphocytes derived from an allogeneic donor. The alloactivated cells are surgically implanted at the tumor site, and produce a mixture of cytokines which induce a primary immune response. During this reaction, the host lymphoid cells identify both the graft lymphoid cells and tumor tissue as foreign.

SUMMARY OF THE INVENTION

The present invention provides compositions and methods for treating a tumor or eliciting an anti-tumor immunological response in a human patient. The compositions contain a combination of cells that are allogeneic to the subject being treated, at least one of which has been alloactivated in culture. The compositions are designed for implantation into the tumor bed of the patient, where they evoke a local reaction with a long-term beneficial effect on the tumor.

Certain embodiments of the invention relate to methods for preparing a pharmaceutical composition containing alloactivated human donor lymphocytes for treating a tumor in a human patient, comprising the steps of (a) coculturing lymphocytes from a first human donor allogeneic to the patient, and leukocytes from a second human donor allogeneic to both the first human donor and the patient, so as to alloactivate the lymphocytes; (b) harvesting the cells and preparing them for human administration at a time when they are effective in the treatment of the tumor. The alloactivated cells are typically harvested from culture near the time of peak cytokine secretion, and are typically effective when given as a single dose.

Also embodied are pharmaceutical compositions prepared according to the aforementioned methods, in some forms containing approximately $2 \times 10^9$ to $2 \times 10^{10}$ alloactivated cells. The pharmaceutical compositions are suitable for human use after washing substantially free of substances like growth factors and serum inappropriate for administration, and in substantially sterile condition.

Also embodied is a cell population containing lymphocytes from a first human that are alloactivated against leukocytes from a second human, for use in a method of treatment of a third human by surgery or therapy. Optionally, the cell population contains leukocytes from at least three different humans. The cell populations can be used in a medicament for treatment of a tumor or raising an anti-tumor immune response in a human patient. The medicament is implanted at the site of a solid tumor, with or without prior resection or partial resection.

Also embodied are methods for treating a tumor in a human patient or raising an anti-tumor immune response, comprising implanting in or around the bed of a solid tumor in the patient a cell population comprising alloactivated human lymphocytes, the cell population having been produced by coculturing lymphocytes from a first human donor ex vivo with leukocytes from a second human donor allogeneic to both the first human donor and the patient. The effect can optionally be boosted by implanting a second alloactivated cell population or administering a cellular vaccine.

Potential benefits of administering the compositions of this invention include limiting the extent of tumor growth, improving quality of life, or extending the median life expectancy.

DETAILED DESCRIPTION

This invention provides therapeutic compositions for use in cancer treatment. The compositions contain live cells, and confer a long-term benefit to human cancer patients when administered into a solid tumor mass.

Figure 1:
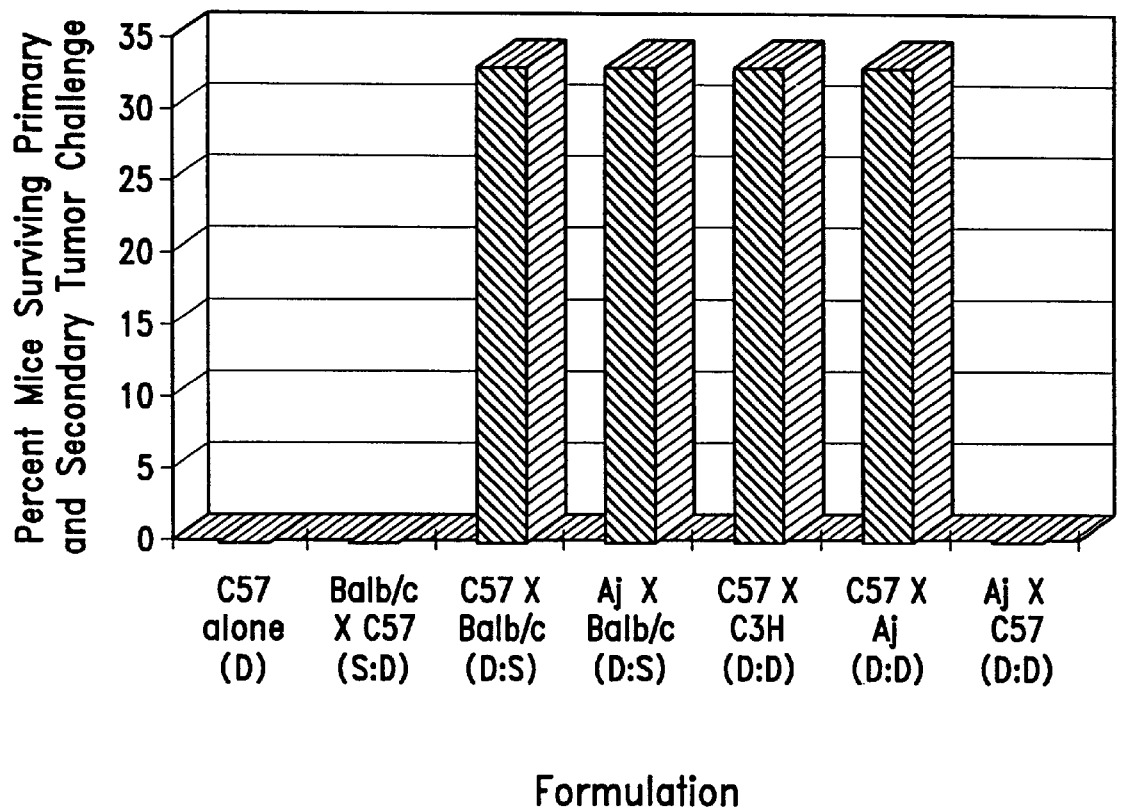
FIG. 1 is a bar graph showing the effect of different alloactivated lymphocyte preparations on providing resistance to a secondary challenge with J588L lymphoma cells in Balb/c mice. Allogeneic cells stimulated either with syngeneic splenocytes or certain third-party splenocytes are both effective.

The results of an instructive experiment are shown in FIG. 1. Balb/c mice were treated with a histocompatible lymphoma and an alloactivated cell population. When the lymphocytes in the population have been against host alloantigens (C57×Balb/c or Aj×Balb/c), a proportion of the mice clear the first dose of lymphoma cells. Some surviving mice are sufficiently well protected to survive a second challenge with the lymphoma cells, consistent with ongoing specific immunity against tumor antigens. It has now been discovered that lymphocytes activated against alloantigens unrelated to those of the treated subject (C57×Aj) are also effective in conferring survival from tumor challenge.

Thus, cells from one donor can be alloactivated against alloantigens a second donor, and still be effective when administered into the tumor bed in a subject who is unrelated to either donor.

The invention shares several features with the method for treating tumors described in International Patent Application WO 96/29394. The live cells in the composition of the present invention include lymphocytes that are allogeneic to the subject being treated, and which have been alloactivated before use in treatment. The cells are implanted directly in or around a solid tumor mass in the patient, with or without resection or partial resection of the tumor.

A key difference is the alloantigens that the lymphocytes in the composition have been activated against. In the WO 96/29394 application, the lymphocytes are activated using leukocytes of the patient to be treated, and are therefore primed specifically against the alloantigens of the patient. In the present invention, the lymphocytes are activated against alloantigens of a second unrelated donor. The donor is invariably allogeneic to the patient at a number of loci for both class I and class II histocompatibility antigens. As a consequence, the lymphocytes are typically not primed specifically against alloantigens of the intended recipient.

Not all third party responder:stimulator cell combinations are equally effective in generating a strong alloreaction. This disclosure provides a number of strategies for overcoming relatively less active combinations.

One strategy is a number of screening assays to measure the extent of alloactivation early in culture. These are detailed in Example 3. Preferred cell populations for use in this invention are those that show a high degree of alloactivation within the first three days, as measured by one or more of the screening assays. This permits various donor-:donor cell populations to be screened in advance of use in therapy.

A second strategy is to use a plurality of third party donors as a source of responder cells, stimulator cells, or both. This is illustrated in Example 5. Using a plurality of donors helps ensure that at least some histoincompatibilities will lead to sufficient alloactivation, as measured in the screening assays. In addition, it has been found that cultures prepared with leukocytes from three or more donors can achieve higher overall levels of alloactivation.

A third strategy is to include in the alloactivation culture an H2 receptor antagonist such as cimetidine. This is also illustrated in Example 5. The use of H2 receptor antagonists brings certain relatively inactive cell combinations over the threshold to measurable alloactivation, and increases the extent of alloactivation in others.

The present invention confers a number of advantages in comparison with previously known technology. For example, it is sometimes is difficult to get enough patient leukocytes to use as stimulators for preparing alloactivated cells. This invention provides that leukocytes from unrelated healthy donors can be used instead, thereby providing an almost limitless supply. In addition, particular donor combinations that generate high levels of alloactivation can be identified in advance, and used to provide a reliable source of effective material. Alloactivated cells may be stored or produced on an ongoing basis, eliminating the necessity of withholding treatment for the two to three days necessary to alloactivate lymphocytes using leukocytes of the patient.

A further description of preferred methods to prepare and use the compositions of this invention are provided in the sections that follow.

DEFINITIONS

"Mixed lymphocyte reaction", "mixed lymphocyte culture", "MLR", and "MLC" are used interchangeably to refer to a mixture comprising a minimum of two different cell populations that are allotypically different. At least one of the allotypically different cells is a lymphocyte. The cells are cultured together for a time and under suitable conditions to result in the stimulation of the lymphocytes. A frequent objective of an MLC is to provide allogeneic stimulation such as may initiate proliferation of the lymphocytes; but unless indicated, proliferation during the culture is not required. In the proper context, these terms may alternatively refer to a mixture of cells derived from such a culture. When cells from an MLC are administered as a bolus to a human, especially in a tumor bed, it is referred to as a "cytoimplant".

The terms "vaccine", "immunogen", or "immunogenic composition" are used herein to refer to a compound or composition, as appropriate, that is capable of either: a) generating an immune response against an antigen (such as a tumor antigen) in a naive individual; or b) reconstituting, boosting, or maintaining an immune response in an individual. The immunological response may comprise antibodies, immunoreactive cells (such as helper/inducer or cytotoxic cells), or any combination thereof, and is preferably directed towards an antigen that is present on a tumor towards which the treatment is directed.

A "cell line" or "cell culture" denotes higher eukaryotic cells grown or maintained in vitro. It is understood that the descendants of a cell may not be completely identical (either morphologically, genotypically, or phenotypically) to the parent cell.

"Inactivation" of a cell is used herein to indicate that the cell has been rendered incapable of cell division to form progeny. The cell may nonetheless be capable of response to stimulus, or biosynthesis and/or secretion of cell products such as cytokines. Methods of inactivation are known in the art. Preferred methods of inactivation are treatment with toxins such as mitomycin C, or irradiation. Cells that have been fixed or permeabilized and are incapable of division are also examples of inactivated cells.

The term "cancer cell", used either in the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells.

The term "tumor-associated antigen" or "TAA" refers to a molecule, complex, or epitope that is detected at a higher frequency or density by tumor cells than by non-tumor cells of the same tissue type. Knowledge of the existence or characteristics of a particular tumor-associated antigen target is not necessary for the practice of the invention.

As used herein, "treatment" refers to clinical intervention in an attempt to alter the natural course of the individual or cell being treated, and may be performed either for prophylaxis or during the course of clinical pathology. Desirable effects include preventing occurrence or recurrence of disease, alleviation of symptoms, diminishment of any direct or indirect pathological consequences of the disease, preventing metastasis, lowering the rate of disease progression, amelioration or palliation of the disease state, and remission or improved prognosis.

The "pathology" associated with a disease condition is anything that compromises the well-being, normal physiology, or quality of life of the affected individual. This may involve (but is not limited to) destructive invasion of affected tissues into previously unaffected areas, growth at the expense of normal tissue function, irregular or suppressed biological activity, aggravation or suppression of an inflammatory or immunological response, increased susceptibility to other pathogenic organisms or agents, and undesirable clinical symptoms such as pain, fever, nausea, fatigue, mood alterations, and such other features as may be determined by an attending physician.

An "effective amount" is an amount sufficient to effect a beneficial or desired clinical result, particularly the generation of an immune response, or noticeable improvement in clinical condition. An immunogenic amount is an amount sufficient in the subject group being treated (either diseased or not) sufficient to elicit an immunological response, which may comprise either a humoral response, a cellular response, or both. In terms of clinical response for subjects bearing a neoplastic disease, an effective amount is amount sufficient to palliate, ameliorate, stabilize, reverse or slow progression of the disease, or otherwise reduce pathological consequences of the disease. An effective amount may be given in single or divided doses. Preferred quantities and cell ratios for use in an effective amount are given elsewhere in this disclosure.

An "individual" or "subject" is a vertebrate, preferably a mammal, more preferably a human. Non-human mammals include, but are not limited to, farm animals, sport animals, and pets.

GENERAL TECHNIQUES

The practice of the present invention will employ, unless otherwise indicated, conventional techniques of molecular biology, microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991). See also Gately et al., Lee et al., and Zarling et al. (infra) for examples of techniques in mixed lymphocyte cultures.

General procedures for the preparation and administration of pharmaceutical compositions are outlined in *Remington's Pharmaceutical Sciences 18th Edition* (1990), E. W. Martin ed., Mack Publishing Co., Pa.

There are a number of animal models for cancer that can be used to test and adjust the compositions and methods of this invention, if desired. Certain models involve injecting in-bred animals with established syngeneic tumor lines. The tumors can be co-injected with a potentially therapeutic composition, allowed to establish before therapy is commenced, or administered as a challenge at some time following vaccination of a naive animal. Illustrations are provided in the Example section. Also usefull are chimeric animal models, described in U.S. Pat. Nos. 5,663,481, 5,602,305 and 5,476,993; EP application 379,554; and International application WO 91/01760.

All patents, patent applications, articles and publications mentioned herein, both supra and infra, are hereby incorporated herein by reference.

PREPARATION OF ALLOACTIVATED CELL POPULATIONS

The cellular compositions of this invention are prepared by alloactivating one or more responder cell populations containing lymphocytes with one or more stimulator cell populations expressing alloantigens. The source of the responder and stimulator cells are allogeneic both to each other, and to the patient to be treated with the resultant composition.

Source of Donor Cells

The cells that are used to prepare the composition are typically taken from healthy unrelated human donors allogeneic to the subject to be treated.

Cells are generally described as allogeneic if they are from the same species but bear a phenotypic difference sufficient to stimulate an alloreaction. In the context of this disclosure, use of the term "allogeneic" is restricted to a difference in phenotype of major histocompatibility complex (MHC) antigens. Any qualitative difference in the identity of MHC allotypes between cells of the same species means they are allogeneic cells. In humans, differences at any of the HLA-A, B, C, D, DP, DQ, and DR loci constitute allotypic differences relevant for this invention. Identity of HLA-A, B, C, DP, DQ, and DR are typically determined using allotype-specific antibodies in a cytotoxicity or immunofluorescence technique.

Preferred allotypic differences for the purposes of the present invention relate to HLA class II antigens. Comparing the class II antigens of the DP, DQ, and DR loci between the putative allogeneic cells and cells of the subject to be treated, preferably at least 1, and increasingly more preferably 2, 3, 4, 5, or even 6 loci are different between allogeneic cells. Class II antigens may also be determined at the D locus by mixed lymphocyte reaction using typed cells. Donors of allogeneic cells are generally unrelated to the subject being treated, to maximize the number of MHC mismatches. In a normal outbred population, unrelated individuals will almost invariably differ at a number of different loci.

The number of class II region mismatches is related but secondary to a functional determination of allogenicity. Allogeneic cells are particularly suitable for use in the present invention if they demonstrate a strong proliferative response when tested in alloreactive cultures. Donors of cells previously known or empirically shown to produce a particularly strong response are especially suitable for use in therapy. As described elsewhere in this disclosure, a panel of different allogeneic cells can be tested in combinations to determine those that elicit the strongest degree of alloactivation.

The "responder" cells are capable of specifically reacting to an allogeneic stimulus. The cell population generally contains lymphocyte cells or cells of the lymphocyte lineage, particularly T cells. Lymphocytes expressing CD4 antigen (CD4+ cells), and cells expressing CD8 antigen (CD8+ cells) are both included in the definition of T lymphocytes, and either or both may be included in the composition. Generally, the responder cells are leukocytes obtained from peripheral blood, typically enriched for mononuclear cells (PBMC), and optionally further enriched for cells of the lymphocyte lineage. Particular enriched populations contain at least 10% CD4+ cells or 10% helper/inducer cells; more preferably they are at least about 20% of CD4+ or helper/inducer cells; even more preferably the portion is at least about 30% of CD4+ or helper/inducer cells. CD4+ cells may be conveniently quantified with commercially available specific antibody such as OKT4 in conjunction with fluorescence-activated counting. However, standard peripheral blood mononuclear cell preparations are suitably enriched for many applications of this invention. Assays for determining the extent of alloactivation are described in the next section.

The "stimulator" cells are allogeneic to the responder cells and capable of eliciting an alloreaction in the responders. Suitable cell types for use as stimulator cells are those that bear a high density of allogeneic histocompatibility antigens, particularly class II antigens. Any type of cell (not limited to blood cells) bearing sufficient alloantigens can be used. A particularly suitable source is peripheral blood leukocytes or white cells. It is desirable to enrich for, or at least not to deplete cells expressing class II histocompatibility antigens from the population, such as B cells and monocytes. Extensive subfractionation of the cells is not usually required, and a simple peripheral blood mononuclear cell population (PBMC) is adequate for most purposes.

The combined cell population is not necessarily restricted to one source for the responder cells and one source for the stimulator cells. Two, three, for, or a higher plurality donors may optionally be used to facilitate collection of the allogeneic cells, to increase stimulation of the allogeneic cells, to minimize the elicitation of an anti-allotype response, or to otherwise enhance the therapeutic efficacy.

Collection and Preparation of Donor Cells

Donors are typically prescreened to identify those with sufficient leukocyte count, and exclude those with neoplastic conditions or transmissible infections. Collection may be performed by whole blood donation followed by separation of blood cell populations, or by leukapheresis. Leukapheresis is especially appropriate for collecting the responder cell population, because the number of cells required is substantial. Sufficient blood is processed to obtain about 100–500 mL leukapheresis suspension, preferably at least about 200 mL. For example, leukapheresis may be performed using a Cobe 2997 (COBE SPECTRAL®, Lakewood CO); Fenwall CS 300 (Fenwall, Deerfield Ill.); or Haemonetrics (Braintree Mass.) blood cell separator. Flow rates of ~40–50 mL/min for 2–4 h yield ~200–250 mL leukapheresis suspension having <1 mL red cells, with variations between individual donors and the equipment used.

The collected leukocytes are generally washed to remove platelets, and resuspended in a suitable medium, such as AIM V supplemented with 2% inactivated fetal calf serum. Separation of PBMC and other enrichment procedures include centrifugation over a suitable medium such as FICOLL™ or HISTOPAQUE®, passage over a nylon-wool column, affinity separation methods such as panning, or sorting in a fluorescent cell sorter using an antibody against a relevant cell-surface marker. Where possible, it is generally preferable to decrease the number of manipulation steps. For example, better leukapheresis separation may obviate the need for subsequent separation on FICOLL™.

Mixed Lymphocyte Cultures

Responder and stimulator cells are combined in a suitable culture medium, typically supplemented with fetal calf serum or a serum substitute, and optionally including other growth factors. The ratio of responder:stimulator cells is preferably between about 100:1 to 1:10; more preferably about 50:1 to 1:1; still more preferably about 20:1 to 5:1, and even more preferably about 10:1. Where there are a plurality of stimulator or responder cells in a one-way MLC, the same approximate ratio of responders:stimulators is maintained. Thus, when using 2 inactivated stimulators, the ratio may be approximately 9:(1:1); when using 3 inactivated stimulators, the ratio may be approximately 8:(1:1:1). Similarly, when using multiple responders, the ratio may be (5:5):1 or (3:3:3):1. If cultured together, the multiple responder composition becomes a multi-way MLC. One-way activation of multiple responders can be achieved by conducting a separate culture for each responder population at a 10:1 ratio, and then combining the alloactivated cells just before use.

This invention encompasses the use of two-way or multi-way mixed lymphocyte cultures, wherein a plurality of cell populations act as both responders and stimulators. In certain embodiments of the invention, one-way MLCs are performed by inactivating the stimulator cells, for example, by treating ~$10^7$ cells/nL with 50 $\mu$g/mL mitomycin C or sublethal irradiation, followed by washing.

Once combined in the desired ratio, the cells cultured at an appropriate density in a suitable atmosphere (such as 95% $O_2$, 5% $CO_2$ at about 37° C.). The culture period is preferably at least about 12 h, more preferably between about 24 h and 72 h. Additional stimulation may be obtained by culturing for 3–5 days, although this is generally not preferred, since cytokine levels are normally higher during the first 48 to 72 h of culture.

The recitation within this disclosure of preferred cell sources, cell ratios, culture conditions, timing, and other features, is intended as an aid to the practitioner and is not meant to limit the scope of the invention, unless explicitly required. No limitation is implied with respect to any of the individual parameters, since various other parameter combinations will generate a cell population with the desired functional effect.

Measuring Functional Criteria of the Alloactivated Cell Population

Once the culture is initiated but before use in therapy, the functional activity of the culture can be determined using one or more functional assays.

Since cytokine secretion is believed to play an important role in eliciting the response in the treated subject, cytokines can be tested in a standard immunoassay. Particular cytokines of interest are IL-2, IL-4, IL-6, TNF-$\alpha$, LT, IFN-$\gamma$, G-CSF, M-CSF (both membrane and secreted form), and GM-CSF. For example, particular degrees of stimulation is indicated by levels of biological activity of TNF-$\alpha$ or LT at 50–150 U/mL, or 500–3500 pg/ml.

Proxies for functional activity of the alloactivated cells include: I: MTT Formazan Reduction Assay; II: XTT Formazan Reduction Assay; III: Flow Cytometry for CD3/CD69 or CD3/FDA; IV: FDA Plate Assay; V: Acid Production Assay, VI: Acridine Orange Assay. These assays are detailed in Example 3. More traditionally, alloactivation can be determined by cell proliferation, measured by culturing a test sample for 5 days and conducting a standard [$^3$H]-thymidine uptake assay, or by counting blast cells. The predictive value of functional assays can be determined by comparing results of the assays on cultured cells with the effect of the cells in a suitable animal model. See Example 4.

Preferred cultures are those that show a level of activation $\geq$10% above unstimulated donor control value within one of the first 3 days of culture, as measured by the Tetrazolium Reduction Assay (XTT), the Acridine Orange Assay (AO) or by Flow Cytometry (CD69), more preferably attaining the threshold in several of these assays in combination.

Optimizing the Functional Effect

Experience in animal model experiments shows that not all third-party donors provide the same degree of alloactivation when third party donor are used for both the stimulator and responder cells.

To the extent that variability is donor-cell dependent, donors can be chosen according to experience, both in terms of the degree of alloactivation observed in culture, and the clinical result. Functional criteria indicating a particular level of activation, such as the Tetrazolium Reduction Assay (XTT), Flow Cytometry Assay, or the level of secretion of certain lymphokines determined by ELISA, may be sufficiently predictive of outcome, depending on clinical experience. Once successful donors are identified, they can be constituted in a panel of regular donors sourced by the service lab providing the immunogenic compositions.

To the extent that the variability depends on the match between donors and patient, several other selection criteria can also be used. Since the efficacy of certain donot-patient combinations may migrate according to histocompatibility, donors can be selected, if desired, on the basis of tissue match. Donors of particular human histocompatibility types can be tested for efficacy with particular tumors, if desired, using one of the chimeric animal models listed earlier. A more immediate donor identification test can be conducted using PBLs from the patient and PBL from a selection of potential donors in an in vitro assay. One such assay is a reverse functional test. In this assay, patients cells are set up in a mixed lymphocyte culture as the responder, using the potential donor of the alloactivated cells as the inactivated stimulator.

Since the response is thought to involve cytokine secretion by the alloactivated cells, an alternative predictor may be a two-stage culture. In this approach, a responder:stimulator culture is set up using the same responder and stimulator cells being tested for use in the preparative culture. At 3 days, the culture is inactivated with mitomycin or sublethal irradiation, so that cells can still produce cytokines but not replicate. Leukocytes from the patient are then added, and their response is followed by a functional assay, cytokine secretion, or T cell proliferation. In a variation of this approach, inactivated tumor cells are also provided in the second stage of the culture, and read-out is determined at the end of the second stage by measuring cytolysis of $^{51}$Cr labeled tumor cells.

These assays are described for the benefit of the reader who may wish to optimize the compositions of this invention in various ways, particularly in setting up a donor panel enriched for high responders. It should be emphasized that the invention can be practiced without employing all of these screening procedures.

As an alternative or in addition to pretesting the responder:stimulator:recipient combination, the degree of alloactivation or the potential therapeutic outcome can be enhanced by employing either of the following strategies: a) using a plurality of donor cells as the responder or stimulator in the MLC; and/or b) adding an H2 receptor antagonist to the culture medium of the MLC.

Using a plurality of donors for the responder or stimulator cell population confers a number of advantages. It is predicted that there will be a normalizing effect—when there is a variety of alloincompatibilities present, there is a stronger possibility that at least one stimulator cell will stimulate at least one responder cell, and in turn, that at least one responder cell will stimulate the treated subject. It is also more convenient, in that the same mixed population will be suitable for a variety of patients. Thus, a large batch of mixed alloactivated cells can be prepared and stored frozen, for dispensation on demand. It has also been discovered that having a plurality of different stimulators can achieve levels of alloactivation higher than one of the stimulators alone. This is illustrated in Example 4.

Adding an H2 receptor antagonist to the culture medium also has an enhancing effect on alloactivation during the first three days of culture. This is illustrated in Example 5. Without intending to be bound by theory, it is hypothesized that the H2 receptor antagonist inhibits the activity of suppressor T cells in the culture. Thus, it is especially effective in restoring alloactivation to cell combinations that are clearly incompatible, but show little reactivity in a standard MLC. A preferred H2 receptor antagonist is cimetidine, added to the culture medium at between 5 µg/mL and 100 µg/mL, typically 20 µg/mL.

USE OF CELLULAR COMPOSITIONS IN CANCER TREATMENT

The compositions of this invention can be administered to subjects, especially human subjects. They are particularly useful for eliciting an immune response against a tumor-associated antigen, or for treating cancer.

Objectives of Treatment

One purpose of implanting the cellular compositions of this invention is to elicit an immune response. The immune response may include either humoral or cellular components, or both. Humoral immunity can be determined by a standard immunoassay for antibody levels in a serum sample from the treated individual.

Since cellular immunity is thought to play an important role in immune surveillance of cancer, generating a cellular immune response is frequently a particular objective of treatment. As used herein, a "cellular immune response" is a response that involves T cells, and can be observed in vitro or in vivo.

A general cellular immune response can be measured as the T cell proliferative activity in cells (particularly PBL) sampled from the subject after administration. Inactivated tumor cells, preferably derived from the subject, are used as stimulators A non-specific mitogen such as PHA serves as a positive control; incubation with an unrelated stimulator cell serves as a negative control. After incubation of the PBMCs with the stimulators for an appropriate period (typically 5 days), [$^{3}$H]thymidine incorporation is measured. If desired, determination of which subset of T cells is proliferating can be performed using flow cytometry. T cell cytotoxicity (CTL) can also be measured. In this test, an enriched T cell population from the subject are used as effectors in a standard $^{51}$Cr release assay. Tumor cells are radiolabeled as targets with about 200 µCi of Na$_2$ $^5$CrO$_4$ for 60 minutes at 37° C., followed by washing. T cells and target cells (~1×10$^4$/well) are then combined at various effector-to-target ratios in 96-well, U-bottom plates. The plates are centrifuged at 100×g for 5 minutes to initiate cell contact, and are incubated for 4–16 hours at 37° C. with 5% CO$_2$. Release of $^{51}$Cr is determined in the supernatant, and compared with targets incubated in the absence of T cells (negative control) or with 0.1% TRITON™ X-100 (positive control).

Another purpose of implanting the cellular compositions of this invention is for treatment of a neoplastic disease, particularly cancer. Beneficial effects are typically immunologically mediated or the result of an inflammatory infiltrate into the injection site and collateral tumors. Evidence of a host response can be shown inter alia by infiltration of host leukocytes (such as lymphocytes, histiocytes, and other leukocytes) into the tumor site by standard histomorphology analysis. The response is preferably an immunological response, which may have humoral or cellular components, and preferably includes cytotoxic T cell activity. Immunological activity can be measured systemically in standard antibody binding immunoassays or cytotoxicity assays on peripheral blood components taken from the treated subject, using tumor cells as targets. Monitoring the effect according to these methods is optional, and the recited features need not be positively demonstrated in order for the compositions and treatment methods to fall within the scope of this invention, except where required.

Suitable Subjects

The compositions of this invention may be used for administration to both human and non-human vertebrates.

Typically, the subject will either have cancer, or be at substantial risk of developing cancer. Typical human subjects for therapy comprise two groups, which may be distinguished by clinical criteria. Patients with "advanced disease" or "high tumor burden" are those who bear a clinically measurable tumor. A clinically measurable tumor is one that can be detected on the basis of tumor mass (e.g., by palpation, MRI, CAT scan, X-ray, or radioscintigraphy; positive biochemical or histopathological markers on their own are insufficient to identify this population).

A cellular composition for use in this invention is administered to patients with advanced disease with the objective of palliating their condition. Ideally, reduction in tumor mass occurs as a result, but any clinical improvement constitutes a benefit. Clinical improvement includes decreased risk or rate of progression or reduction in pathological consequences of the tumor.

A second group of suitable subjects is known in the art as the "adjuvant group". These are individuals who have had a history of cancer, but have been responsive to another mode of therapy. The prior therapy can have included (but is not restricted to) surgical resection, radiotherapy, traditional chemotherapy, and other modes of immunotherapy. As a result, these individuals have no clinically measurable tumor by the definition given above. However, they are suspected of being at risk for recurrence or progression of the disease, either near the original tumor site, or by metastases. The adjuvant group may be further subdivided into high-risk and low-risk individuals. The subdivision is made on the basis of features observed before or after the initial treatment. These features are known in the clinical arts, and are suitably defined for each different cancer. Features typical of high risk subgroups are those in which the tumor has invaded neighboring tissues, or which show involvement of lymph nodes.

A cellular composition for use in this invention is administered to patients in the adjuvant group in order to elicit an anti-cancer response primarily as a prophylactic measure against recurrence. Ideally, the composition delays recurrence of the cancer, or more preferably, reduces the risk of recurrence (i.e., improves the cure rate). Such parameters may be determined in comparison with other patient populations and other modes of therapy.

Of course, crossovers between these two patient groups occur, and the cellular compositions can be administered at any time that is appropriate. For example, therapy can be conducted before or during traditional therapy of a patient with high tumor burden, and continued after the tumor becomes clinically undetectable. Therapy may be continued in a patient who initially fell in the adjuvant group, but is showing signs of recurrence.

Examples of tumors that can be treated according to this invention include but are not limited to those on the following list. The list includes sites that are thought to be immune privileged, such as the brain, and sites that are not immune privileged, such as the pancreas, colon, breast, and prostate.

Brain tumors, such as astrocytoma, oligodendroglioma, ependymoma, medulloblastomas, and PNET (Primitive Neural Ectodermal Tumor);

Pancreatic tumors, such as pancreatic ductal adenocarcinomas.

Lung tumors, such as small and large cell adenocarcinomas, squamous cell carcinoma, and bronchoalveolarcarcinoma; Colon tumors, such as epithelial adenocarcinoma, and liver metastases of these tumors;

Liver tumors, such as hepatoma, and cholangiocarcinoma;

Breast tumors, such as ductal and lobular adenocarcinoma;

Gynecologic tumors, such as squamous and adenocarcinoma of the uterine cervix, and uterine and ovarian epithelial adenocarcinoma;

Prostate tumors, such as prostatic adenocarcinoma;

Bladder tumors, such as transitional, squamous cell carcinoma;

Tumors of the RES System, such as B and T cell lymphoma (nodular and diffuse), plasmacytoma and acute and chronic leukemia;

Skin tumors, such as malignant melanoma; and

Soft tissue tumors, such as soft tissue sarcoma and leiomyosarcoma.

The immune status of the individual may be any of the following: The individual may be immunologically naive with respect to certain tumor-associated antigens present in the composition, in which case the compositions may be given to initiate or promote the maturation of an anti-tumor response. The individual may not currently be expressing anti-tumor immunity, but may have immunological memory, particularly T cell memory relating to a tumor-associated antigen, in which case the compositions may be given to stimulate a memory response. The individual may also have active immunity (either humoral or cellular immunity, or both) to a tumor-associated antigen, in which case the compositions may be given to maintain, boost, or maturate the response, or recruit other arms of the immune system. The subject should be at least partly immunocompetent, so as to minimize a graft versus host reaction of pathological scope. However, it is recognized that cancer patients often show a degree of immunosuppression, and this does not necessarily prevent the use of the compositions of the invention, as long as the compositions may be given safely and effectively.

Modes of Administration and Dose

The compositions of this invention can be administered to the subject at the site of any solid tumor. Circulating cancers are treatable so long as there is at least one solid tumor mass. Metastatic sites, affected nodes, and other sites away from the primary neoplasm are suitable, so long as they are accessible and contain sufficient tumor antigen.

If the solid tumor mass is resectable or partly resectable, then the composition can be administered at or near the site or in a cavity created by the resection. If the tumor is completely removed, however, then it may be preferable to administer the alloactivated cells to a metastatic site to increase the local amount of bystander tumor antigen. The most convenient time to administer the alloactivated cells to a resectable site is during the time of surgery. To keep the cells at the site until completion of the surgical procedure, it is convenient to administer the cells in a pharmaceutically compatible artificial gel, or in clotted plasma.

When the solid tumor mass is not resectable, or where less invasive procedures are desired, then the composition can be injected at or near the tumor site through a needle. For deeper sites, the needle can be positioned using ultrasound, radioscintigraphy, or some other imaging technique, alone or in combination with the use of an appropriate scope or cannula. Pancreatic tumors are preferably implanted using an injection needle positioned by an endoscopic ultrasound guided technique, as described by Chang et al., *Gastroenterology* 112:A346, 1996 (abstract). For this application, the cell population is conveniently administered when suspended in isotonic saline or a neutral buffer to a volume of about 10 mL.

The dose given is an amount "effective" in bringing about a desired therapeutic response, be it the stimulation of an immune response, or the treatment of cancer as defined elsewhere in this disclosure. For the pharmaceutical compositions of this invention, effective doses typically fall within the range of about $10^8$ to $10^{11}$ cells, including allogeneic stimulators and responders. Preferably, between about $1 \times 10^9$ to $5 \times 10^{10}$ cells are used; more preferably between about $2 \times 10^9$ to $2 \times 10^{10}$. Multiple doses when used in combination to achieve a desired effect each fall within the definition of an effective amount.

The various components of the implant composition are present in an "effective combination", which means that there are sufficient amounts of each of the components for the composition to be effective. Preferably, at least about $10^8$, more preferably between about $1 \times 10^9$ to $5 \times 10^{10}$ and; more preferably between about $2 \times 10^9$ to $2 \times 10^{10}$ responder cells are present. Preferably, at least about $10^7$, more preferably between about $5 \times 10^7$ to $5 \times 10^9$ and; more preferably between about $1 \times 10^8$ to $2 \times 10^9$ stimulator cells are present. Ratios of allogeneic lymphocytes to stimulator leukocytes is generally between 1:1 and 100:1, usually between about 5:1 and about 25:1, and typically about 10:1. However, any number of component cells or other constituents may be used, as long as the composition is effective as a whole. This will also depend culture conditions and other factors during preparation.

The pharmaceutical compositions of this invention may be given following, preceding, in lieu of, or in combination with, other therapies relating to generating an immune response or treating cancer in the subject. For example, the subject may previously or concurrently be treated by chemotherapy, radiation therapy, and other forms of immunotherapy and adoptive transfer. Where such modalities are used, they are preferably employed in a way or at a time that does not interfere with the immunogenicity of the compositions of this invention. The subject may also have been administered another vaccine or other composition in order to stimulate an immune response. Such alternative compositions may include tumor antigen vaccines, nucleic acid vaccines encoding tumor antigens, anti-idiotype vaccines, and other types of cellular vaccines, including cytokine-expressing tumor cell lines.

Certain embodiments of this invention relate to combination therapies. In one preferred combination therapy, the subject is given an intra-tumor implant of stimulated allogeneic lymphocytes, either before, during, or after treatment at a site distant from the tumor with a composition comprising stimulated allogeneic lymphocytes and autologous tumor cells. The preparation and use of vaccines of this nature is described in detail in International application WO 98/16238, which is hereby incorporated herein by reference in its entirety. An illustrative protocol for this combination therapy is provided in Example 6. In the illustration, the vaccine is given weekly for four weeks following the cytoimplant, to enhance the extent of the anti-tumor response in the host or the therapeutic effectiveness. The vaccine can also be given after intervals of several months in order to replenish the response. Accordingly, certain embodiments of this invention relate to administering a cytoimplant, and subsequently boosting the therapeutic effect or immunological response by administering to the patient a composition comprising alloactivated human lymphocytes allogeneic to the patient and an inactivated cell population consisting of tumor cells from the patient or progeny thereof.

While the methods and compositions of this invention are generally effective when given at a single dose, it may be desirable to readminister the composition at intervals of 3–6 months, especially for fast-growing tumors that can be injected through a positioned needle. Accordingly, certain embodiments of this invention relate to administering a cytoimplant, and subsequently boosting the therapeutic effect or immunological response by implanting in or around the bed of a solid tumor in the patient a second cell population comprising alloactivated human lymphocytes allogeneic to the patient.

Timing of administration of compositions of this invention is within the judgment of the managing physician, and depends on the clinical condition of the patient, the objectives of treatment, and concurrent therapies also being administered. Suitable means of immunological monitoring include a one-way MLR using patient's PBL as responders and primary tumor cells as stimulators. An immunological reaction may also be manifest by a delayed inflammatory response at the injection site. Suitable means of monitoring of the tumor are selected depending on the tumor type and characteristics, and may include CT scan, magnetic resonance imaging (MRI), radioscintigraphy with a suitable imaging agent, monitoring of circulating tumor marker antigens, and the subject's clinical response. Additional doses may be given, such as on a monthly or weekly basis, until the desired effect is achieved. Thereafter, and particularly when the immunological or clinical benefit appears to subside, additional booster or maintenance doses may be given as required.

When multiple cytoimplants or combinations of implants and cellular vaccines are given to the same patient, some attention should be paid to the possibility that the allogeneic lymphocytes in the vaccine may generate an anti-allotype response. The use of a mixture of allogeneic cells from a plurality of donors, and the use of different allogeneic cell populations in each dose, are both strategies that can help minimize the occurrence of an anti-allotype response.

During the course of therapy, the subject is evaluated on a regular basis for general side effects such as a febrile response. Side effects are managed with appropriate supportive clinical care.

The examples presented below are provided as a further guide to a practitioner of ordinary skill in the art, and are not meant to be limiting in any way.

EXAMPLES

Example 1

MIXED LYMPHOCYTE CULTURE PROCEDURE.

Collection of Responder PBMC from Unrelated Donor

Peripheral blood mononuclear cells (PBMCs) were collected by leukapheresis from normal healthy donors unrelated to the patient to be treated. Donors were pre-screened to test for complete blood count (CBC) with differential, Hepatitis A, B, and C, VDRL, and HIV-I.

Approximately 150 to 300 ml of leukapheresis suspension containing PBMC was collected from each donor, using standard blood donation procedures for supportive apheresis according to the manufacturers' instructions. The leukapheresis was performed using a Fenwall CS 3000 (Deerfield, EL) blood cell separator. A flow rate of 40 to 50 ml/min for 2 to 4 hours with lymphocyte yield of $2-4 \times 10^9$ processed a total donor blood volume of 7,000 to 12,000 ml to yield 200 to 250 ml of leukapheresis suspension having less than 1 ml of red cells. If a Cobe 2997 blood cell separator was used, the centrifuge rate was 5×g, the flow rate was up to 45 ml/min, and the collection rate was no more than or equal to 2.5 mil/min.

However, if donor pre-absolute lymphocyte counts were in the $0.6 \times 10^9$ to $1.0 \times 10^9$ range, as little as 150 ml of leukapheresis product was drawn. Hematocrit for the final product was 3.5%. At least one total blood volume was processed for 80% efficiency of lymphocyte collection.

The anticoagulant used was either 2% citrate or a citrate/anticoagulant ratio of ACDA—15 ml/citrate—100 ml; ACDB—25 ml/citrate—100 ml; or CPD—14 ml/citrate—100 ml. To obtain the utmost product purity, the actual and final product from the cell separator was transported as a pure concentrate of cells in autologous plasma. The cells were not washed, and no albumin was added.

Preparation of Donor Cells

The leukapheresis product was transported to the MC Oncology Research Laboratory for the production of allogeneic mixed lymphocyte cells (MLCs) for immunotherapy.

Cells were drained from the leukapheresis pack into two or three 250 ml centrifuge tubes, removing and setting aside 3 ml for sterility tests to be done during centrifugation. Cell concentrate was diluted with phosphate buffered saline (PBS) and centrifuged for 7 minutes at 2,000 rpm. Centrifugation was repeated twice for a total of three times to wash the cells free of the clotting factor in the donor's serum.

Three 1 ml aliquots from the 3 ml removed from the leukocyte suspension were placed into sterile capped tubes for sterility testing. The first 1 ml aliquot was added to thioglycollate medium (Difco, Detroit, Mich.) (30–35° C., 48 hr.); a second 1 ml was added to tryptic soy broth (Difco, Detroit, Mich.) (25–30° C., 48 hr.); and the third 1 ml was added to RPMI 1640 (GIBCO, Gaithersburg, Md.) with 10% heat inactivated FBS (RPMI-10%) and 1% L-glutamine, but without antibiotics.

Cells were spin washed twice at 150 g for 10 minutes in PBS to remove platelets. The supernatant was very carefully discarded as cells were in a slurry and not a pellet. Cells were resuspended in AIM V (GIBCO, Gaithersburg, Md.) supplemented with 2% heat inactivated FBS (2% AIM V) to 420 ml, and placed into a T-175 $CM^2$ flask.

Patient or donor blood was diluted 1:1 with sterile saline. For cell separation, 35 ml of cell suspension was carefully layered onto 15 ml Histopaque® g 1.077 suspension medium (Sigma, St. Louis, Mo.) in each 50 ml tube and centrifuged at 250 g for 45 minutes. Centrifugation was started slowly and gradually increased to full speed. After centrifugation, the interface containing mononuclear cells between the Histopaque® suspension medium and the plasma layer was carefully collected with a 25 ml sterile pipet deposited into clean 50 ml centrifuge tubes, diluted with 2% AIM V Media 1:1, and centrifuged at 550 g for 7 to 10 minutes to form a cell pellet. Cells remained a minimum of time in the Histopaque® suspension medium, because it is toxic to the cells.

The supernatant was discarded, the pellet was resuspended in 2% AIM V and divided into two 50 ml centrifuge tubes to a total volume 40 ml, and centrifuged at 550 g for 5 minutes. After washing, the supernatant was discarded. The washing step was repeated twice for a total of three times. After the last wash, cells in each tube were resuspended in 50 ml of 2% AIM V. Aliquots of 1 ml of the resuspended cells were diluted to a ratio of 1:10 in 2% AIM V per tube, then further diluted 1:1 in Trypan Blue (Sigma, St. Louis, Mo.) to distinguish dead from live cells, and the live cells were counted in a hemocytometer. Cells were set at $2 \times 10^6$/ml with 2% AIM V.

Collection of Stimulator PBMC from Tumor Patients

From 200 to 400 ml of peripheral blood cells were drawn from glioblastoma patients by vena puncture and placed into 250 ml centrifuge tubes, removing and setting aside 3 ml for sterility tests to be done during spinning. Blood cells in the centrifuge tubes were diluted with saline and centrifuged for 7 minutes at 550 g. Centrifugation was repeated twice for a total of three times to wash the cells free of the clotting factor in the patient's serum. Sterility testing was conducted as described above.

Cells were washed twice by centrifugation at 150 g for 10 minutes in saline to remove platelets, the supernatant was very carefully discarded, and 420 ml of cells were resuspended in a T-175 $CM^2$ flask in saline.

15 ml of Histopaque® 1.077 cell separation medium was added to twelve 50 ml centrifuge tubes, and 35 ml of cells suspended in saline were layered onto the Histopaque® 1.077 in each 50 ml tube. The cell suspensions were spun at 250 g for 45 minutes, starting centrifugation slowly and gradually increasing speed.

After centrifugation, the mononuclear cells at the interface between the Histopaque® cell separation medium and the plasma layer were carefully collected with a 25 sterile pipet into 2 sterile 250 ml centrifuge tubes and diluted with 2% AIM V to a fmal volume of 250 ml. The diluted mononuclear cells were centrifuged at 550 g for 7 to 10 minutes. For washing, the supernatant was discarded, then the cell pellet was re-suspended with 2% AIM V and centrifuged at 550 g for 5 minutes. The washing step was repeated for a total of three times.

After the last washing step, cells were re-suspended in 50 ml of 2% AIM V, 1 ml of the cell suspension was diluted 1:10 in 2% AIM V per tube, and the number of viable cells was determined by enumeration in a 1:1 in Trypan Blue as described above.

It is readily appreciated that this procedure is equally suitable for obtaining stimulator cells from healthy third-party donors.

Alloactivation

The isolated patient PBMCs were re-suspended at $10^7$ cells/ml in AIM V, 50 $\mu g$ Mitomycin C (Bristol-Mayer Squibb, Princeton, N.J.) were added per ml of patient cell suspension, and the suspension of PBMCs was incubated at 37° C. for one hour to block response of the stimulator cells to the responder cells. After one hour of incubation, the excess mitomycin C was washed from the cells by alternate centrifugation (250 g for 5 min), and the cells were resuspended in AIM-V. After mitomycin treatment of the patient's PBMCs, the cells were added at a 20:1 to 10:1 donor cell:patient cell ratio to the donor culture).

For co-culture, the donor and mitomycin C-treated patient PBMC suspension was placed in a sealed sterile Fenwal tissue culture system especially designed for culture of PBMC for reimplantation into patients. Cells were passed in sealed systems via Fenwal cell transfer units and pumps according to the manufacturers instructions, and cultured in a 37° C. incubator for 48 hours.

Sterility Testing of Alloactivated Cells

Two days prior to implantation of the cell suspension, the following three sterility tests were performed. 10 ml sterile aliquots were removed from each tissue culture bag, placed into sterile capped 15 ml centrifuge tubes, and centrifuged for 10 minutes at 450 g. In each tube, the pellet was resuspended in 3.0 ml of PBS. A 1 ml aliquot of the cell suspension was added to each of three sterile capped tubes containing 2 ml of thioglycollate broth, tryptic soy broth, or RPMI-10% and incubated for 48 hours. Each cell suspension was examined microscopically prior to implant to detect signs of microbial growth.

On the day of surgery, the cells were centrifuged out of their medium, washed two times with saline and re-suspended in platelet free, decalcified plasma obtained from the patient the previous day. The cells were transported to the operating room in plasma, then the plasma was re-calcified by the addition of calciun gluconate so that it clots just before implantation into the tumor bed.

The day of surgery a drop of collected cell pellet was again examined for sterility under the microscope. Just prior to clotting, a 100 $\mu l$ aliquot of the cell suspension was added to 2 ml each of RPMI-10% without antibiotics, thioglycollate and tryptic soy broth in a sterile capped tube. The samples were then incubated for four days after surgery, and a running log was kept of this last sterility test.

Example 2

CLINICAL TRIAL USING ALLOACTIVATED CELLS IMPLANTED AT THE TUMOR SITES

This experiment confirms that allogeneic cells alloactivated using patient leukocytes are effective in cancer treatment.

A Phase I/II clinical trial was conducted to examine the feasibility, tolerability, toxicities and clinical effects associated with a single intratumoral injection of allogeneic lymphocytes sensitized against patient alloantigens. This trial is conducted under the auspices of the appropriate ethical approval committee, and in accordance with a protocol under the U.S. Food & Drug Administration.

Eligible patients were men and women between 18 and 85 years of age. A total of ten patients were studied. Eight patients were enrolled in the trial, and two additional patients were treated off-study on a compassionate basis. Nine of ten patients had locally advanced, surgically unresectable pancreatic tumors; 40% of the patients had Stage II disease, 30% had Stage III disease and 20% had Stage IV disease. One patient with Stage I disease was 89 years old, declined surgery and was treated on a compassionate basis. Seven of ten patients had received no prior therapy, one patient had received prior radiation therapy and two patients had received prior radiation and chemotherapy.

Preparation of Cells

The procedure for preparing the cytoimplant cells was generally in accordance with the main features of Example 1. Typically, a volunteer third-party donor for responder cells is screened by normal blood bank criteria for suitability. No special matching or identification of HLA type is performed. Whole blood or leukapheresis is collected from the patient to be treated; and leukapheresis is collected from the donor on the same day. Mononuclear cells are prepared from both patient and donor by centrifigation on Ficoll™, and counted to ensure that enough cells are present to prepare the intended dose. Patient cells are inactivated by treating for 1 hour with mitomycin C, and then washed.

The cells are combined at a donor:patient ratio of 10:1 to 20:1, depending on the number of patient cells available. The cells are suspended at $3 \times 10^6$ per mL in AIM 5 medium containing 2% fetal calf serum and antibiotics in a gas-permeable plastic bag, and incubated at 37° C. in an atmosphere of 5% $CO_2$/95% $O_2$. No cytokines or other growth factors are added. After three days, the cells are collected by centrifugation and washed. The cells are then transferred to the clinic in a medium suitable for administration. For the treatment of pancreatic cancer, the cells were suspended in a volume of about 10 mL isotonic saline.

Features of the cells are shown on the following table:

TABLE 1

Alloactivated Cells Administered to Humans with Pancreatic Cancer

| Patient | MLC Cell Ratio | Total Cell Dosage | Final Viability | Final Sterility | MLC CD3/** CD69 | MLC IL-2 (ng/mL)+ | MLC INF-γ (ng/mL)+ |
|---|---|---|---|---|---|---|---|
| 001, LM | 10:1 | $1.76 \times 10^{9*}$ | 91% | Sterile | NA | 2779 | 202 |
| 002, SA | 10:1 | $3.5 \times 10^9$ | 98% | Sterile | 11.8% | 10852 | 438 |
| 003, RW | 10:1 | $2.8 \times 10^9$ | 88% | Sterile | NA | 2334 | 383 |
| 004, OY | 20:1 | $5.9 \times 10^9$ | 92% | Sterile | NA | 1927 | 0 |
| 005, MR | 10:1 | $6.0 \times 10^9$ | 95% | Sterile | NA | 3941 | 298 |
| 006, OB | 20:1 | $6.04 \times 10^9$ | 96% | Sterile | NA | 118 | 0 |
| 007, BS | 10:1 | $5.8 \times 10^9$ | 93% | Sterile | NA | 7307 | 981 |
| 008, LM | 10:1 | $8.9 \times 10^9$ | 91% | Sterile | 18.6% | 1137 | 308 |
| 009, GS | 13:1 | $10.5 \times 10^9$ | 95% | Sterile | NA | 433 | 0 |
| 010, JH | 15:1 | $9.6 \times 10^9$ | 90% | Sterile | NA | 11858 | 291 |

Administration

The treatment was conducted as follows: A sufficient amount of whole blood or leukapheresis was collected from each patient to prepare the cultured cells used in treatment. The sample was forwarded to the Immunotherapy Lab, and used to prepare stimulator cells for allogeneic stimulation of third-party lymphocytes.

Three days later the cytoimplant cells were administered to the subject on an out-patient basis. Under light anesthesia, an injection needle was positioned into the tumor using an endoscopic ultrasound guided technique. The implant cells were rescued from culture, washed, suspended in about 10 mL of injectable isotonic saline, and delivered to the diagnostic service center. The cells were injected into the tumor mass, the device was removed, and the patient was allowed to recover.

Three patients were administered with a single dose of $3 \times 10^9$ implant cells. Four patients were administered with a single dose of $6 \times 10^9$ implant cells. Three patients were administered with a single dose of $9 \times 10^9$ implant cells.

Follow-up was done one day, one week, one month, and every three months after implantation. Criteria assessed included evidence of toxicity, survival, tumor response (endoscopic ultrasound and/or CT-scan), tumor markers (CEA/CA19-9) and Karnofsky performance score.

Results

Patients treated with $3 \times 10^9$ cells: Patient 001 was a 78 year old male with an unresectable clinical Stage IV tumor. The patient received treatment on a compassionate basis, and survived 6.5 months. Patient 002 was a 53 year old female with an unresectable Stage III tumor. The patient later presented with elevated total bilirubin and died at 4.2 months after developing liver metastasis. Patient 003 was a 60 year old male with unresectable Stage III tumor. There was a hospital admission for synocopal episode. The patient survived 20.8 months.

Patients treated with $6 \times 10^9$ cells: Patient 004 was a 52 year old male with an unresectable Stage II tumor. The patient was later admitted to hospital with biliary obstruction, cholangitis, and dehydration. This patient died 20.7 months after treatment. Patient 005 was an 89 year old female with a Stage I tumor, who was not a candidate for resection due to her age. She received treatment on a compassionate basis, and died 11.3 months later due to myocardial infarction. Patient 006 is a 54 year old female with an unresectable Stage III tumor. She was later admitted to hospital for intractable nausea, vomiting and dehydration, and subsequently for gastrointestinal hemorrhage. There was increased tumor size and liver metastasis. The patient died 4.3 months after treatment. Patient 007 is a 61 year old female with an unresectable Stage II tumor. On follow-up, there was elevated total bilirubin, and the patient was admitted with intractable nausea and vomiting, diarrhea, and dehydration, possibly related to colitis flare-up. The patient is still xalive >13 months after treatment.

Patients treated with $9 \times 10^9$ cells: Patient 008 is a 55 year old female with an unresectable Stage IV tumor. No serious adverse events were observed, and the patient is still alive >13 months after treatment. Patient 009 is a 54 year old male with an unresectable Stage II tumor. The patient was later admitted for two days for pain and nausea and vomiting. The patient died 11.7 months after treatment. Patient 010 is a 68 year old male with an unresectable Stage II tumor. No serious adverse events were observed, and the patient died 8.5 months after treatment.

Clinical Interpretation

Elevated bilirubin, liver enzymes and nausea/vomiting with dehydration were the most common serious adverse events documented which were considered to be due to obstruction of biliary stents. These adverse events were considered to be associated with the disease rather than the therapy. Because of its relationship to the timing of the administration of the cytoimplant, one adverse event (elevated total bilirubin, Grade 4) was considered possibly related to therapy. No other serious adverse effects were observed that were considered to be associated with therapy.

The median survival for all patients treated in this study was 11.5 months (range 4.2 to >21) with a mean survival of greater than 10 months. The 6 month, 9 month, and 12 month probability of survival was 80% (n=8), 60% (n=6), and 50% (n=5), respectively. The probability of greater than eight month survival by dose was 33% for $3 \times 10^9$ cells, 75% for $6 \times 10^9$ cells, and 100% for $9 \times 10^9$ cells. Comparison of median survivals of patients treated with cytoimplant to those treated with 5-fluorouracyl (median=4.2 months) or GEMZAR™ (median=5.7 months) was significant at $p<0.006$ and $p<0.004$, respectively.

Histomorphology

Histology slides were prepared from tissue samples from an 89 year old female diagnosed with pancreatic adenocarcinoma. At the time of diagnosis, the tumor was advanced and surgically unresectable. The only treatment performed on this patient was the injection of the tumor with $6 \times 10^9$ cytoimplant cells. The patient died of a myocardial infarct 11.5 months later.

One photomicrograph showed fibrovascular tissue with scattered individualized tumor cells. There is a dense lymphocytic and plasma cell infiltrate. Another field showed lymphocytes rosetting the separated tumor cells. The tumor cells were dark and shrunken, which is evidence of apoptosis. Another field showed scattered islands of necrotic tumor cells. There was a very dense infiltrate of lymphocytes, and lymphocytes appear to be trafficking into the site from adjacent venules. In a high magnification view there was clear evidence of direct contact between lymphocytes and necrotic tumor cells.

The histomorphology analysis provide clear evidence of a local response by cells of the patient after implantation of the alloactivated cells. The data are consistent with the cell response in the patient having a direct role in the beneficial effects of the treatment, as shown by direct contact between lymphocytes and necrotic tumor cells. To the limited extent that infiltrating cells are present in untreated pancreatic cancer, this type of direct contact is not observed.

Example 3

MEASUREMENT OF THE DEGREE OF ALLOACTIVATION

In order to ensure the production of high quality effective MLC cells, a method of measuring the potency of the alloactivated cells can be employed. Only cell cultures with activity over and above unstimulated control cells should be used clinically. It is beneficial to compare the activity to the unstimulated control, since baseline activity of mononuclear cells from different individuals varies widely.

Several methods are available for measuring lymphocyte activation. Compared with unstimulated mononuclear cells, alloactivated cells reduce more Formazan dye and have more esterase activity. Turnover of XTT (a Formazan dye) can be easily demonstrated in a 96-well plate by colorimetric spectrophotometry at 470 nm (reference 650 nm). Activated cells typically show higher absorbance than controls. Lymphocyte activation can also be demonstrated by flow cytometric determination of esterase activity using the esterase substrate, fluorescein diacetate (FDA). T cells with high esterase are not determined using FDA and a Phycoerythrin-labeled CD3 antibody. Esterase activity can be accurately measured in a plate assay by using higher concentrations of FDA and determination of esterase activity by spectrophotometry at 494 nm (reference 650 nm) in a 96-well plate format. Background esterase activity inherent to serum-containing media is inhibited by addition of a competitive esterase inhibitor (~10 mM), arginine methyl ester. For the most part, these measures show good correlation with each other and with blastogenesis.

I: MTT Formazan Reduction Assay

This assay is used to enumerate live cells by ability for culture sample to reduce MTT to blue-green Formnazan dye, and is also helpful for the distinguishing activated from inactive cells. It can be used for practically any cell in practically any media. The usefil cell range is between $10^5$ and $5 \times 10^6$ per mL.

Reagents:

96 well plates, flat bottom (not ELISA plates)

5 mg/mL MTT (Sigma) in PBS (frozen)

20% SDS in 45% DMF, 0.2 N HCl (pre-warmed to 37° C.)

Procedure:

Place 100 μL of culture media with cells in 96 well plate in duplicate or triplicate. Use 100 μL of media alone for controls. Leave first column blank.

Add 10 μL of MTT to each well. Tap plate to mix. Cover plate and incubate 37° C. for 4 hours.

Add 50 μL of SDS solution, avoiding bubbles. Tap to mix. If bubbles are present, blow on surface. Count plate at 570 nm (reference 650 nm).

II: XTT Formazan Reduction Assay

This assay is used to enumerate live cells by ability for culture to sample to reduce XTT to red-orange Formazan dye, and is also helpful for the distinguishing activated from inactive cells. It can be used for practically any cell in practically any media. The usefull cell range is between $10^5$ and $5 \times 10^6$ per mL.

Reagents:

96 well plates, flat bottom (not ELISA plates)

1 mg/mL MTT (2,3-bis(2-methoxy-4-nitro-5-sulfo-phenyl-2H-tetrasolium-5-carboxanilinide salt, Sigma) in PBS (fresh)

1.53 mg/mL PMS (phenylmethanesulfonyl fluoride, Sigma) in PBS (frozen, protected from light)

Procedure:

Place 100 μL of culture media with cells in 96 well plate in duplicate or triplicate. Use 100 μL of media alone for controls. Leave first column blank.

Pre-mix PMS with XTT immediately before use (5 μL per mL XTT). Add 50 μL of XTT to each well. Tap plate to mix.

Cover plate and incubate 37° C. for 4 hours. Count plate at 470 nm (reference 650 nm).

III: Flow Cytometry for CD3/CD69 or CD3/FDA

This is a measurement of T lymphocyte activation after mixed lymphocyte alloactivation. Activities such as CD69 expression or esterase activity correlate with cytokine secretion and can be used as surrogate measures of lymphocyte activity. Unstimulated lymphocytes do not express surface CD69 and have only low levels of non-specific esterases. Once activated by alloantigens or non-specific mitogens, the expression of CD69 appears within 48 hours (peak at 24). Esterase activity increases shortly after stimulation, and continues for several days. Not all allostimulated lymphocyte reactions proceed with the same kinetics, and it is preferable to measure activation on day 1, 2 and 3 of the culture.

Sample:

Test samples of donor and patient cells are mixed in small cultures at $0.5 \times 10^6$ cells/mL in 2% FCS-RPMI. These cultures are maintained at 37° C. in 5% $CO_2$ incubator until testing.

Reagents:

Monoclonal antibodies:

CD3-PE (Coulter)

CD69-FITC (Becton-Dickinson). Keep refrigerated when not in use and protect from light.

Fluorescein Diacetate (Sigma): Stock solution is prepared at 10 mg/mL DMSO, protected from light, and stored in frozen lot tested aliquots. Make working solution weekly by diluting stock 1:100 in DMSO, keep working solution refrigerated and protected from light.

D-PBS, 0.5% paraformaldehyde-0.05% TRITON™ X-100 in PBS

Procedure:

Internal control unstimulated and activated mononuclear cells samples are produced on an as-needed basis. Large lot-tested batches will be frozen in 250 μl aliquots in 10% DMSO freezing media.

Mononuclear cells from a normal donors can be used to produce activated control specimens. These cells are placed in 2% FCS-RPMI at $0.5 \times 10^6$ cells/mL up to 100 mL. Cells are cultured for 2 days at 37° C. in the presence or absence of 2 μg/mL PHA lectin, or admixed at a ratio of 10:1 with a second donor population. The cells are collected by centrifugation at 350×g for 5 minutes. The media is removed and replaced by 1/10th the volume of DMSO Freezing media, and frozen. When needed, control unstimulated and stimulated cells can be thawed quickly and resuspended at the original volume by adding 9 volumes of PBS.

Control cells are analyzed according to the protocol below along with samples from the test culture. The duplicate use of control specimens is an addition quality assurance measure. The percentage of CD69 or esterase positive lymphocytes should be within a 5% variance.

Dilute 5 μL of CD3-PE antibody (per sample) in 0.5 mL PBS (per sample). Add either 10 μL CD69 (per sample) or 1 μL of working solution of FDA (per sample).

To 12×75 mm labeled polystyrene tubes, deliver 0.5 mL of diluted antibody. Add 100 μL of well mixed sample to each tube, including reference controls, unstimulated donor cells and the allo-activated cells. Gently vortex and incubate 30 minutes at room temperature. Add 0.5 mL of 0.5% paraformaldehyde-0.05% TRITON™ X-100 PBS and mix.

Counting is performed on an appropriately equipped flow cytometer, such as the EPICS XL Coulter Flow Cytometer. Histogram 1 (forward scatter vs. CD3) of either protocol should have a generous gate around the CD3+ mononuclear cells. Region A should approximate % T-Lymphocytes and should be passed to Histogram 2. In Histogram 2, the use of side scatter versus CD3 permits discrimination of lymphocytes (low side scatter level) from unlysed RBSs, RBC ghosts, platelet aggregates, residual granulocytes and/or other debris. A gate is drawn around the lymphocytes (see Histogram 2 for example). This second gate is passed to Histogram 3, where the CD3+ CD69+ cells or CD3+ FDA+ cells are displayed. Run the control values first to set gates (unstimulated controls). Place the quad stat cursor of Histogram 3 so that the CD69 or FDA high values (Quad 2) are 2%. Leave this gate set when analyzing stimulated samples.

Count at least 5,000 gated cells for each sample to obtain a 97% confidence interval.

IV: FDA Plate Assay

This assay is used to enumerate live cells by ability for culture sample to turnover the esterase substrate, fluorescein diacetate, and is also helpful for the distinguishing activated from inactivated cells. This assay can be used for practically any media. The useful cell range is between $10^5$ and $5 \times 10^6$ per mL.

Reagents:

96 well plates, flat bottom (not ELISA plates)

10 mg/mL FDA (Sigma) in DMSO (stock, protect from light)

10 mg/mL Arginine methyl ester (Sigma) in DMSO

Procedure:

Place 100 μL of culture media with cells in 96 well plate in duplicate or triplicate. Use 100 μL of media alone for controls.

Make a fresh working solution of FDA by adding 10 μL per mL of PBS of stock FDA plus 50 μL AME stock per mL. Add 20 μL of FDA working solution to each well. Tap plate to mix.

Cover plate and incubate 37° C. for 1 hour. Count plate at 494 nm (reference 650 nm).

V: Acid Production Assay

This assay is used to quantitative relative organic acid production in cultures. This correlates with the state of activation of cells. This assay requires the use of medium containing no more than 2% serum. Practical cell range is $1-5 \times 10^6$ cells/mL incubated from 24–48 hours.

Reagents:

96 well plates, flat bottom (not ELISA plates)

Acid Analysis Reagent. This is made in bulk and stored at 4° C. Add 0.1 mg/mL Bromophenol Blue in distilled water. Add sufficient concentrated HCl until the appropriate titration point is met. Titration is performed until yellow-green color is obtained after adding 75 μL of reagent to 100 μL RPMI 2% FCS in a well of a 96 well plate.

Procedure:

Place 100 μL of culture media with cells in 96 well plate in duplicate or triplicate. Use 100 μL of media alone for controls.

Add 75 μL of Reagent to each well. Tap plate to mix. Count plate at 470 nm (reference 650 nm).

VI: Blastogenesis Quantitation

This assay is used to quantitate the absolute number of lymphoblasts produced in cultures after 7 days. The usefull cell range is between $1 \times 10^5$ and $5 \times 10^6$ per mL. Place 1–2 drops of a 7 day culture in a Cytospin chamber and perform Cytospin. Stain dried glass slide with either Wright's Stain or Diff-Quick Stain. Count number of lymphoblasts and other cells under oil immersion 100X lens of microscope. Count over 300 total cells.

In an alternative procedure, spleen cells are cultured in 5×75 mm polypropylene tubes identical to the AO test. After 7 days at 37° C., the cells are mixed by vortexing and a cytospin preparation is made (Shandon cytocentrifuge,). The slides are stained with Wright/Giemsa stain using an automated slide stainer and the blasts enumerated manually by counting at least 300 cells/slide. The percent blasts is calculated by dividing the number of blasts by the total number of nucleated cells.

VII: Cell Proliferation Assay

[$H^3$]-Thymidine incorporation into DNA is measured as follows: Responder spleen cells are suspended at 1 million cells/ml in RPMI-1640 containing 10% fetal bovine serum, antibiotics (streptomycin/penicillin) and $5 \times 10^{-5}$ M 2-Mercaptoethanol. One hundred ul of these cells are seeded in triplicate wells of a u-bottom microtiter plate (Costar). Stimulator spleen cells are then prepared identical to responder spleen cells but are irradiated with 3000 ($Cs^{137}$ source) prior to use. One hundred ul of the stimulator cells are added and the mixed lymphocyte culture is incubated at 37° C. for 7 days in a 95% air/5% $CO_2$ atmosphere. After 7 days 10 ul of $H^3$-thymidine (0.5 mCi/ml, ICN Pharmaceuticals, Costa Mesa, Calif.) is added to each well for 6 hours. The microtiter plate is then harvested used a MASH harvestor and the amount of incorporated thymidine determined by counting the harvested wells in a liquid scintillation counter. The stimulation index (SI) is then determined by calculating the ratio of the CPM of H3-Thymidine incorporated into the MLC culture divided by the CPM of H3-thymidine incorporated into the control (unstimulated) culture.

VIII: Acridine Orange Incorporation

Potency determination is conducted by incorporation of Acridine Orange (AO): Spleen cells are cultured at 1 million/ml in the same media as the cell proliferation assay but in 5×75 mm polypropylene tubes. Each tube receives 1 ml of reaction mixture. After 3 to 7 days of incubation at 37° C., the tubes are mixed by vortexing, and 200 ul removed and placed in a fresh 5×75 mm polypropylene tube. 50 ul of acridine orange (50 mg/ml in PBS) is then added for 15 minutes at room temperature. The tubes are again mixed by vortexing and the cells analyzed for the incorporation of acridine orange by flow cytometry. Results are expressed as the ratio of fluorescence intensity of samples of MLC activated cells versus samples of control (inactivated) cells.

Example 4

ANIMAL MODELING OF IMPLANT THERAPY

Efficacy of Alloactivated Cells Prepared using Third-party Stimulators

Cell compositions were prepared, composed of either unstimulated allogeneic cells alone, allo-activated syngeneic cells, syn-activated allogeneic cells or alloactivated allogeneic cells (two separate allogeneic cells), or all-activated allogeneic cells (two separate allogeneic donors). Splenocytes form the mice were used to produce the alloactivated cells by culturing at a ratio of 10:1 responder:stimulator cells. Splenocyte combinations were cultured in RPMI plus 10% fetal calf serum (FCS) supplemented with penicillin-streptomycin at $3 \times 10^6$/mL at 37° C. for 3 days.

$1 \times 10^6$ live J588L lymphoma cells were admixed with $10 \times 10^6$ cultured mouse splenocytes, and then injected into the subcutaneous tissue over the right flank of Balb/c mice. Treated mice were watched for tumor growth for 3 weeks.

Mice without tumor were rechallenged 1 month later with $1 \times 10^6$ live lymphoma cells alone by left flank subcutaneous injections, and watched for tumor growth.

FIG. 1 shows the results of these experiments. The presence of activated allogeneic cells correlates with a subsequent in vivo antitumor host response. Cell populations prepared using two donors allogeneic to the treated animal could be used in place of syngeneic or autologous cells in order to induce an antitumor response. However, not all combinations of activated allogeneic Donor:Donor cell populations were equally effective.

Effect of Ratio of Responder:Stimulator Cells on Efficacy

Cell populations were prepared composed of allogeneic cells activated by a variable number of syngeneic stimulator cells, using C57 splenocytes as the responder and Balb/c splenocytes as the stimulator. The cells were admixed with live lymphoma cells (J588L cells) and injected into the flanks of Balb/c mice. Treated mice were watched for tumor growth for 3 weeks.

Figure 2:
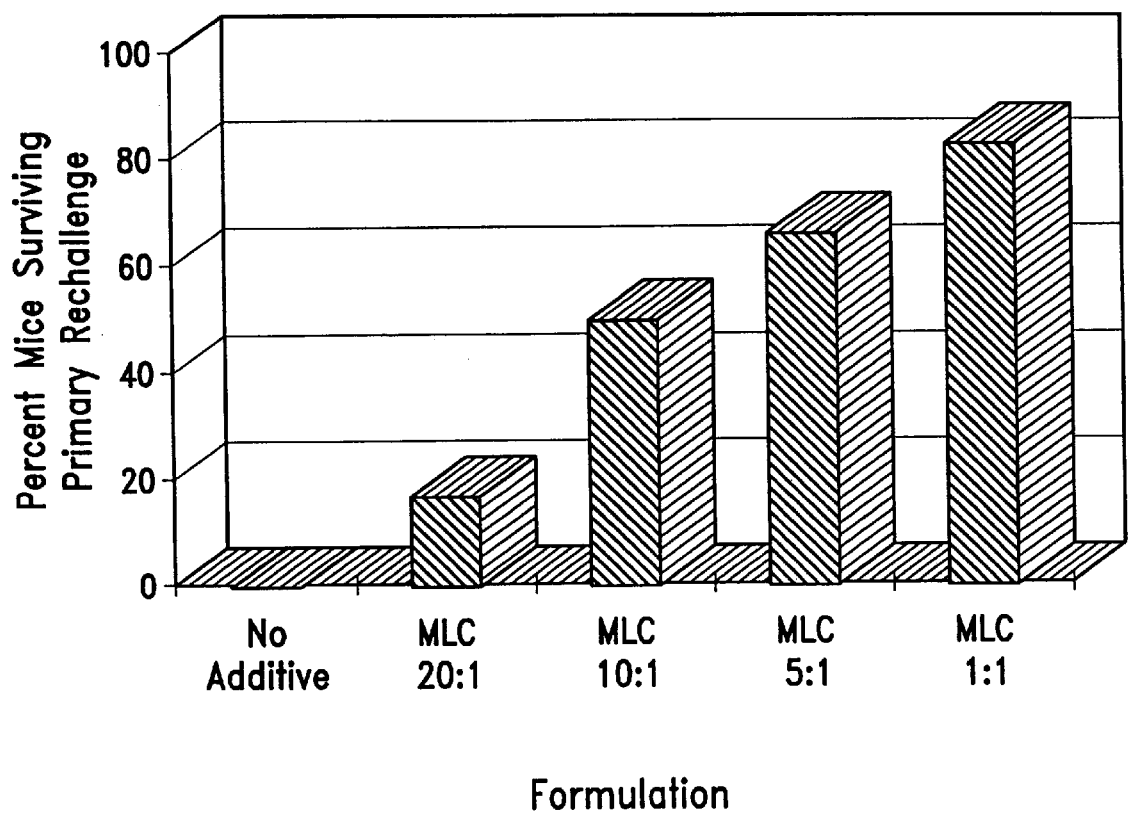
FIG. 2 is a bar graph showing the effect of different cell culture ratios on survival time in the mouse lymphoma model.

FIG. 2 shows the percentage of mice without tumors after primary tumor challenge (6 mice per group). A lower cell ratio may on some occasions be better at inducing an antitumor response in mice.

Impact of Using Splenocytes from Tumor-Bearing Mice on the Antitumor Effect

Splenocytes were taken from naive C57 or Balb/c mice or from a mouse bearing a 1 cm lymphoma in the right flank. The cells were cultured for 3 days either alone or after admixture with Balb/c cells at a 10:1 ratio at a concentration of $0.5 \times 10^6$ cells/mL in RPMI-10% FCS. Lymphocyte activation was judged by analyzing the percentage of CD3+/Esterase high population by Flow Cytometry. The percent FDA positive cells was 3.5% using stimulators from healthy Balb/c donors, but only ~2.5% using stimulators from tumor-bearing donors.

The cell populations alloactivated with stimulators either from naive Balb/c mice or from mice bearing J588L tumors were admixed with live lymphoma cells (J588L cells) and injected into the flanks of naive Balb/c mice. The mice were monitored for tumor growth for 3 weeks. Mice without tumors were next rechallenged with $1 \times 10^6$ live lymphoma cells alone in the left flank, and watched for tumor growth. Percent mice without tumors after secondary tumor challenge was between 30 and 40% in both groups, being slightly higher in the group treated with cells stimulated using naive Balb/c donors.

This indicates that cells obtained from healthy donors are equally effective as stimulators as cells obtained from animals bearing the target tumor.

Resistance of Mice Immunized with Alloactivated Lymphocytes and Irradiated Tumor Cells to Subsequent Tumor Challenge This experiment tested the immunogenic effect of a cell vaccine containing alloactivated lymphocytes mixed with inactivated tumor cells.

C57/BL6 mice (3 per group) were injected subcutaneously with $10^6$ irradiated B16 melanoma cells alone, mixed with $10^7$ Balb/c×C57 alloactivated lymphocytes, or mixed with $10^6$ IL-4 secreting J588L lymphoma cells (allogeneic to C57). The alloactivated cells were prepared by culturing Balb/c splenocytes with C57 splenocytes at a ration of 10:1 at $3 \times 10^6$/mL in RPMI 10% FCS for 3 days.

Cells were washed in PBS, and injected subcutaneously in the flanks of naive C57 mice. After 3 weeks, the mice were rechallenged with 5×10⁵ B16 live melanoma cells subcutaneously in the opposite flank. Mice were observed for tumor formation and sacrificed after tumors reached 1 cm in diameter.

The mice treated with the alloactivated cells survived significantly longer than the other groups. The two longest surviving mice finally developed cone-shaped tumors, both of which ulcerated. No other mice developed ulcers. Two days after the ulcers appeared, both mice expired. Necropsy of these mice revealed the presence of extremely necrotic tumor cells, with evidence of recent tumor cell lysis in the form of massive DNA deposition. This necrosis was accompanied by an inflammatory infiltrate, consisting mostly of lymphocytes. No other form of infection was observed anywhere in the body. No lung metastases were seen. This is in contrast to the large number of lung metastases in control mice harboring B16 melanoma tumors in the flank. Bilateral kidneys in both mice showed extensive glomerulonephritis, suggesting death from tumor lysis syndrome. No other mice demonstrated these changes.

These results are consistent with the mice treated with the alloactivated cell vaccine developing a specific response that caused massive lysis of the live cancer cells given in the subsequent challenge.

In another experiment using a different tumor model, C57/BL6 mice (3 per group) were injected subcutaneously with $10^6$ Lewis Lung carcinoma cells alone, mixed with $10^7$ Balb/c×C57 alloactivated lymphocytes cells, or mixed with $10^6$ IL-4 secreting J588L lymphoma cells (allogeneic to C57). The alloactivated cells were prepared by culturing Balb/c splenocytes with C57 splenocytes at a ratio of 10:1 at $3×10^6$/mL in RPMI 10% FCS for 3 days. All cells were washed in PBS and injected subcutaneously in the flanks of naive C57 mice. Mice were observed for tumor formation, and sacrificed after tumors reached 1 cm in diameter. Mice treated with IL-4 secreting cells survived significantly longer than the other groups with 2 out of 3 long term survivors. The group treated with alloactivated cells alone had no long term survivors.

Correlation of Functional Markers with Antitumor Effect

To determine the correlation between in vitro functional assay results and potential therapeutic benefit, cultures showing various degrees of activation are tested in the mouse lymphoma treatment model. Mixed lymphocyte cultures are set up using splenocytes from a variety of inbred mouse strains at a 10:1 responder:stimulator cell ratio. Alternatively, cultures are set up using a particular responder:stimulator strain combination, but at different cell ratios. After three days of culture, the activity is measured in XTT Formazan assay and esterase assay.

Just before injection, the cultured cells are supplemented with additional splenocytes, as necessary, to normalize the cell ratio, and admixed with $1×10^6$ live or irradiated J588L lymphoma cells. The preparation is the injected into Balb/c mice, and the effect on survival is monitored. The mice can be rechallenged with a subsequent dose of live lymphoma cells to test for a persisting immunological response. The survival data is then correlated with the functional activity measured during the culture period.

Effect of Alloactivated Cell Composition on Antitumor Effect

As described elsewhere in this disclosure, histamine impairs alloactivation during the lymphocyte culture, as measured in the functional assays. Cimetidine, which is an H2 receptor antagonist, promotes alloactivation. In this study, alloactivation cultures are prepared in the presence or absence of 20 µg/mL histidine or cimetidine, tested in the XTT Formazan and esterase assays, and then injected into Balb/c mice with J588L lymphoma cells to correlate with efficacy.

In another study, the effect of having a plurality of different stimulator or responder cells is tested. Standard cultures containing C57:Balb/c splenocytes (10:1) are compared for efficacy in the mouse lymphoma model with cultures containing: a) C57:Aj:Balb/c splenocytes (9:1:1 or 5:5:1); b) C57:Aj:C3H splenocytes (9:1:1 or 5:5:1); c) C57:Aj:C3H:Balb/c splenocytes (8:1:1:1 or 3:3:3:1).

Example 5

EXPERIMENTS WITH CULTURED HUMAN CELLS

Criteria for Functionality of Alloactivated Cells

The degree of alloactivation (a potential reflection of potency in therapy) can be measured according to the functional assays detailed in Example 3. This example illustrates the degree of activation revealed by the assays.

Human peripheral blood monocytes were isolated from samples taken from a number of unrelated human volunteers, and set up in one-way mixed lymphocyte cultures at a 10:1 responder:stimulator ratio as described elsewhere in this disclosure. The assays were run after 2–3 days in culture.

Figure 3:
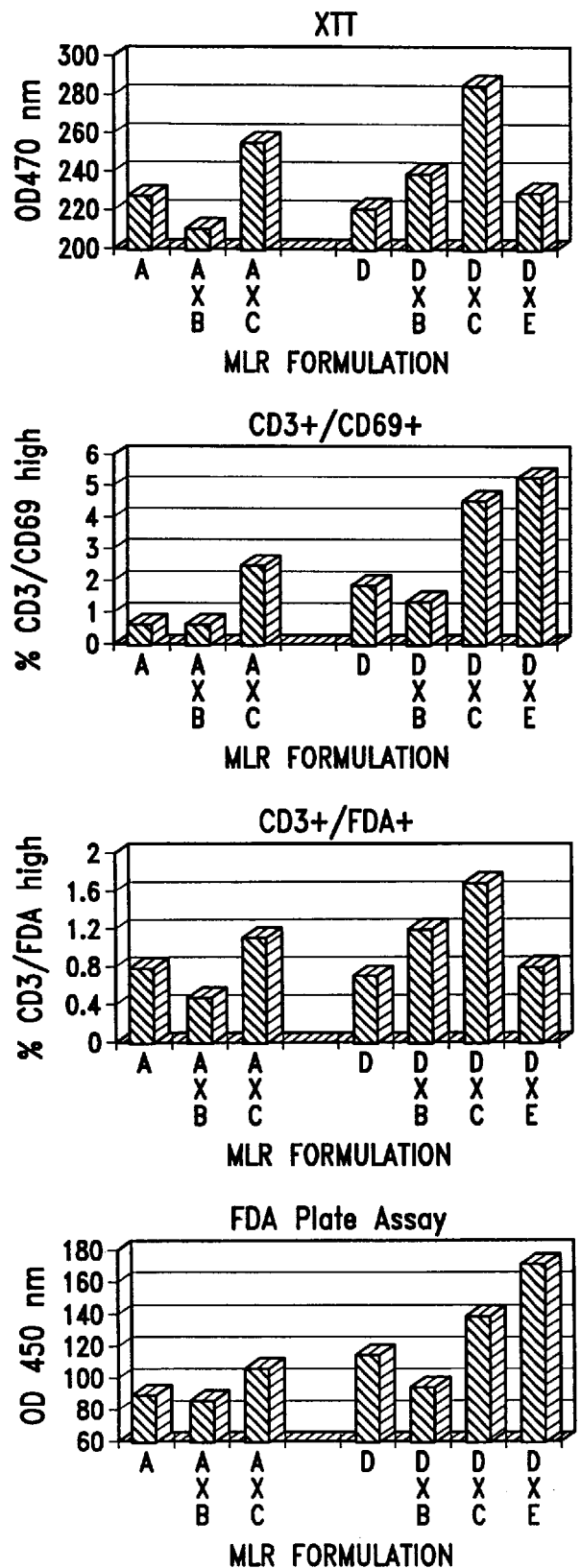
FIG. 3 is a bar graph showing the degree of functional activity in different human alloactivated cell preparations, as determined in four different assays.
Figure 4:
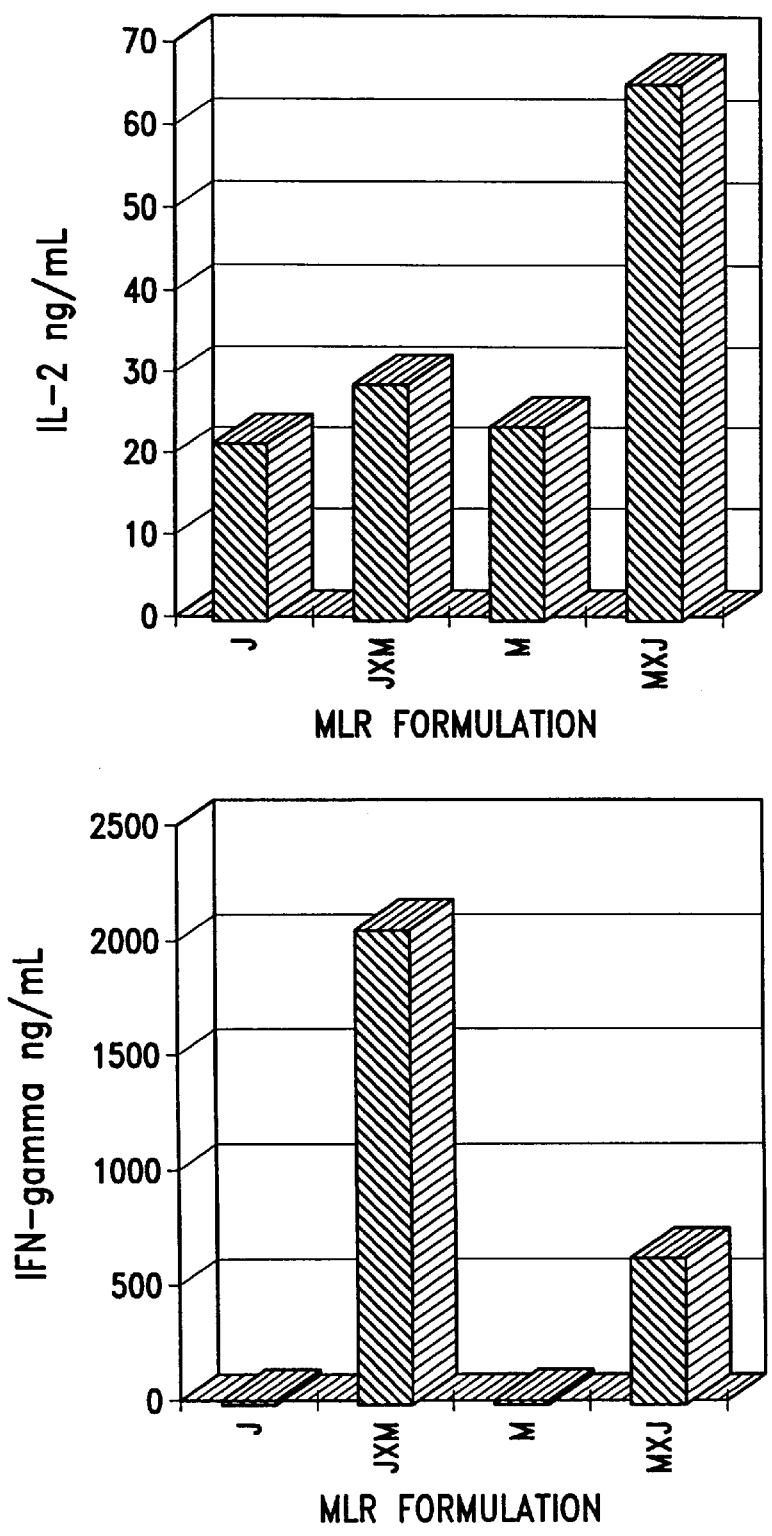
FIG. 4 is a bar graph showing the level of secretion of the cytokines IL-2 and IFN-γ by human alloactivated cell preparations.

The results are shown in FIGS. 3 and 4. Each of the individuals is indicated by a unique letter, with the responder cells being indicated before the stimulator cells. Thus, the designation A×B means that cells from individual A were cultured with inactivated cells from individual B.

Compared with unstimulated mononuclear cells, alloactivated cells have more esterase activity and reduce more XTT (a Formazan dye). Esterase activity can also be measured by flow cytometry using the esterase substrate, fluorescein diacetate (FDA). T cells with high esterase activity can be identified by Phycoerythrin-labeled CD3 antibody in conjunction with FDA. These measures correlate well with blastogenesis (determined after culturing for one week), or the level of IL-2 or IFN-γ in the supernatant.

Impact of Using Multiple Allogeneic Stimulator Cells

Allo-activated human lymphocyte cultures were produced using cells from either one, two, three or four unrelated donors. $3×10^6$ cells/mL were cultured in 2% FCS-RPMI at 37° C. for 2 days. Two-donor populations were produced by admixing responder cells with stimulator cells at a 10:1 ratio. Populations containing three or four donor cells were produced by mixing responder cells with two or three different stimulator cells at ratios of 9:1:1 or 8:1:1:1.

Figure 5:
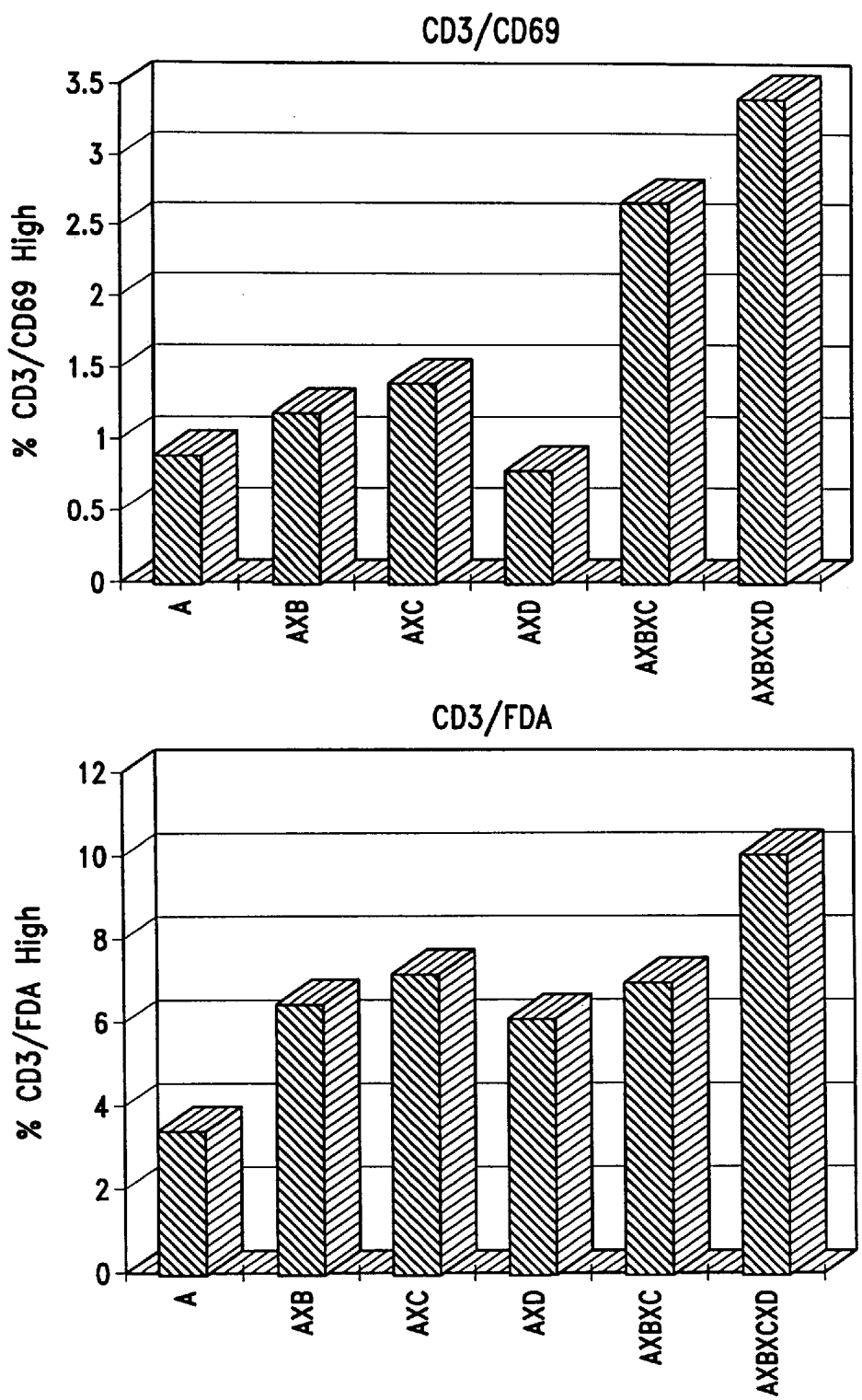
FIG. 5 is a bar graph showing the enhancement of alloactivation of human lymphocytes by using a plurality of different stimulator cells.

FIG. 5 shows the characteristics of the cells measured using flow cytometry. All values represent percentage of brightly fluorescent cells after counting 4000 cells on a Coulter EPICS XL Cytometer.

The results show that cultures prepared with stimulators from a plurality of donors in certain conditions reach higher levels of activation.

Impact of Altering the Ratio of Responder:Stimulator Cells

Mixed lymphocyte cultures composed of allo-activated human peripheral blood mononuclear cells were produced using cells from the same two unrelated donors at ratios of 10:1, 5:1, or 1:1. Cells were cultured at $0.5×10^6$ cells/mL in 2% FCS-RPMI for 3 days. The strength of these cultures was measured using the XTT Formazan reduction assay.

Figure 6:
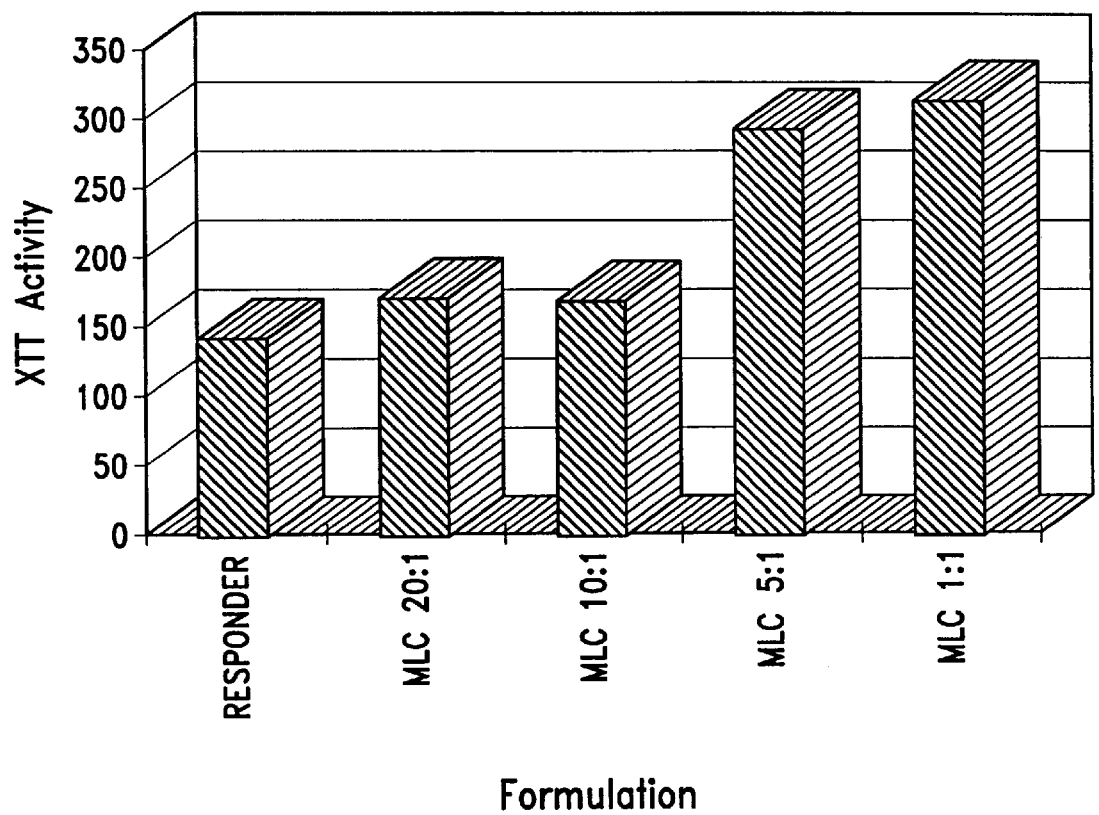
FIG. 6 is a bar graph showing the degree of functional activity of different human alloactivated cell preparations, depending on the ratio of responder:stimulator cells.

The results are shown in FIG. 6

Impact of Histamine or Cimetidine on Alloactivation

Histamine is known to induce the activity of T suppressor cells. Since T suppressor cells can play a role in controlling the activity of the MLR, the effect of histamine and of a potent histamine type 2 (H2) receptor blocking drug, Cimetidine, was tested in alloreacting cell cultures. Cell populations composed of alloactivated human peripheral blood mononuclear cells were produced using cells from unrelated donors. All cultures contain a 10:1 ratio of responder:stimulator mononuclear cells at $0.5 \times 10^6$ cells/mL. In some cultures, 20 µg/mL histamine or 20 µg/mL Cimetidine were added on day 0.

Figure 7:
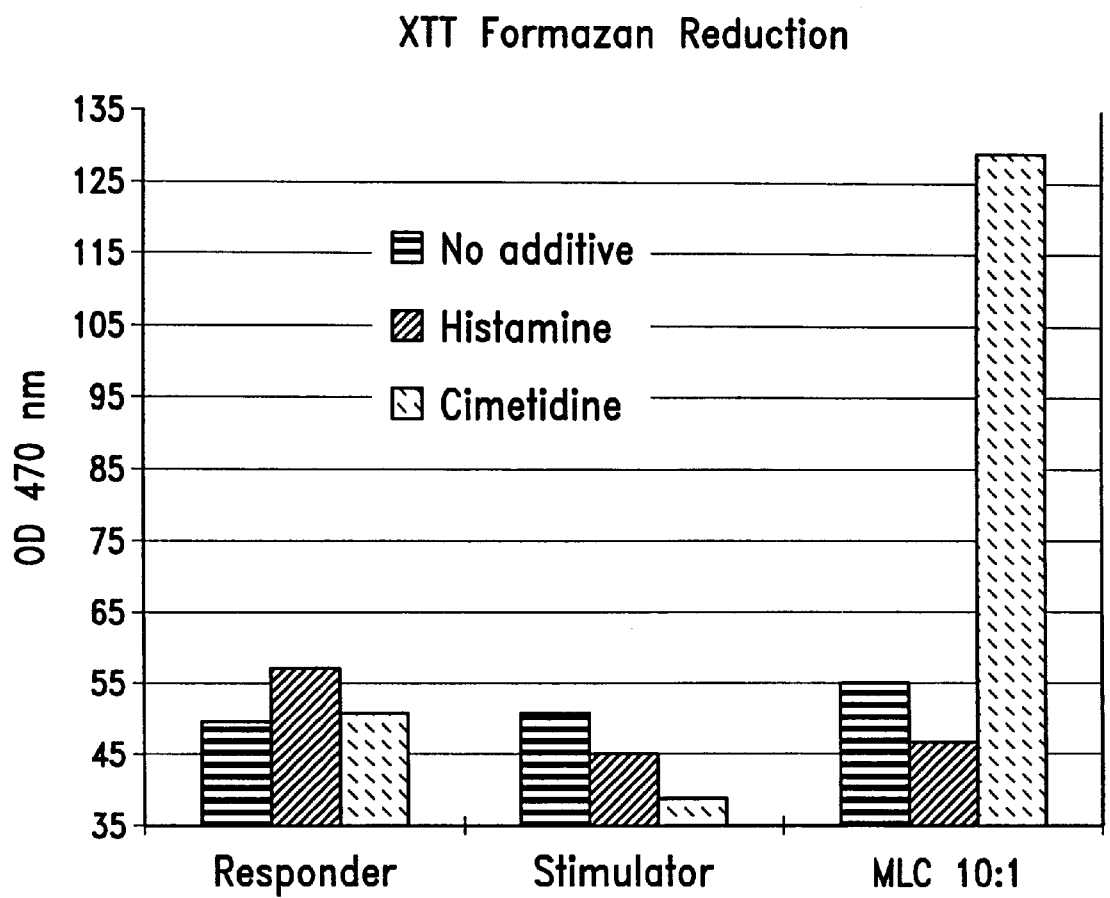
FIG. 7 is a bar graph showing the effect of including 20 µg/mL of histidine (dark shading) or cimetidine (light shading) into cultures of human cells; either the responder alone, the stimulator alone, or mixed cultures at a responder:stimulator ratio of 10:1.

FIG. 7 shows the results measured using a Formazan reduction (XTT) assay.

Histamine induced suppression and decreased strength of the allo-activation. Cimetidine enhanced activity, possibly by blocking the development of suppression.

Example 6

TUMOR REGRESSION ACHIEVED USING STIMULATOR-RESPONDER CELL COMBINATIONS FROM TWO THIRD-PARTY DONORS

This example describes animal experiments in which immunological treatment of established malignant tumors leads to tumor regression and induction of permanent, long lasting tumor specific immunity.

The tumor used in this study is a non-immunogenic glioma histocompatible with the Fischer 344 (F344) rat, designated RT-2 (also known as D74). D74 is an extremely aggressive, transplantable tumor in the F344 rat with histologic and clinical characteristics of Glioblastoma Multiforme. It is essentially incurable by standard therapeutic protocols. Intracranial implantation of as few as 10 cells results in fatal brain tumors in about 40 days. When injected subcutaneously, as few as 500,000 cells form progressively growing tumors, first palpable in about 5 days, then progressing to large, 2 to 3 cm tumors in 3 to 4 weeks. D74 is not immunogenic on its own, as inoculation of naive rats with multiple doses of large numbers of lethally irradiated (10,000 rads) D74 tumor cells does not confer immunity. Surgical removal of well established growing tumors also does not result in subsequent immunity of the host.

Previous studies had established that cytoimplants are effective both in stimulating an anti-cancer immunological response in the treated subjects, and providing a significant clinical improvement. Intratumor implantation of alloactivated cells 10 days after administration of D74 cells resulted in a significant slowing of tumor growth, increasing median survival from 21 to 31 days. Animals receiving a single implant ultimately died of progressive tumor growth. Injection of two successive cytoimplants on Day 10 and Day 17 slowed tumor growth, with 3 out of 5 animals showing essentially complete tumor regression. The response in these animals was found histologically to be accompanied by infiltration of lymphocytes leading to tumor cell apoptosis and necrosis. Animals showing regression of the primary tumors also rejected a D74 parental challenge, indicating that systemic immunity to D74 had been established. The reaction was specific, because challenge with the breast adenocarcinoma line MADB106 led to progressively growing tumors. In another study, animals were treated with two successive cytoimplants and those not showing complete tumor regression had their tumors removed. These animals were also found to be immune to rechallenge with D74 cells in a cell-specific manner.

The current study was designed to test the effect of different donor cell populations in the preparation of the alloactivated cells.

Allogeneic cells were sensitized by in vitro mixed lymphocyte culture (MLC) in the following manner. Spleen cells for use as a source of responder or stimulator lymphocytes were aseptically removed and minced into single cell suspensions in phosphate-buffered saline (PBS). The cells were passed through fine mesh gauze to remove small particulate debris, and washed twice by centrifugation (1500 rpm). The stimulator cells were inactivated by irradiation with 3000 Rads using a $Cs^{137}$ source. Responder cells were cultured at 3 million/mL in RPMI-1640 containing 10% fetal calf serum, antibiotics (streptomycin/penicillin) and $5 \times 10^{-5}$ M β-mercaptoethanol; then stimulated with irradiated spleen cells at a 5:1 responder:stimulator cell ratio. After 3 days at 37° C., the cells were harvested by centrifugation, washed twice in PBS, and suspended in PBS at 500 million/mL. This preparation is referred to in this example as a cytoimplant.

Cytoimplants were administered to F344 rats bearing established (4 to 7 mm) D74 tumors growing in the left thigh. The tumors were initiated approximately 10 days earlier by injecting naive F344 rats subcutaneously with 0.5 million D74 cells suspended in 100 µL PBS. Cytoimplants were suspended in a tuberculin syringe fitted with a 25 gauge needle, and were injected directly into the tumor nodule in a volume of about 100 to 250 µL. Tumor sizes were measured bidirectionally using calipers 2 to 3 times/week, until the tumors reached 3.0 cm, at which time the animals were sacrificed.

The animals received one of several treatment regimens: Group 1 received intratumor injections of 250 µL PBS alone on Days 10 and 17 (control, n=4); Group 2 received intratumor injections of 150 million Wistar anti-F344 cytoimplant cells in 250 µL PBS on both Day 10 and Day 17 (n=5); Group 3 received intratumor injections of Wistar anti-ACI cytoimplant cells on both Day 10 and Day 17 (n=5); Group 4 received an intratumor injection of Wistar anti-ACI cytoimplant cells on Day 10 followed by PVG anti-ACI cytoimplant cells on Day 17 (n=5); Group 5 received an intratumor injection of Lewis anti-ACI cytoimplant cells on both Day 10 and Day 17 (n=5). Thus, Groups 3, 4, and 5 all were treated with cytoimplants made with two donor cell populations from different strains than the F344 tumor-bearing subjects. The Wistar is an outbred rat strain; the others are inbred. All strains are allogeneic at the MHC in comparison with F344 rats, except for the Lewis strain which is syngeneic.

At Day 23 (six days after the second implant), average tumor diameters were as follows: Group 1 (saline control): 20 mm (representing growth of ~2 mm per day); Group 2: 10 mm (down from 12.5 mm on Day 20, statistically significant with respect to Group 1); Group 3: 14 mm (statistically significant with respect to Group 1); Group 4: 15 mm (down from 17 mM on Day 21, with at least one animal showing signs of regression and three showing signs of stabilization); Group 5: 15 mm (with several animals still showing some evidence of tumor progression).

These results show that lymphocytes from a first subject that are alloactivated against leukocytes from a second subject can be used to treat established tumors of a third subject by implantation into the tumor bed. Results in individual subjects treated by the same protocol are heterogeneous. Sequential implants have a synergistic effect, and can lead to not only extended survival, but also tumor regression. Implant cells work well when they are cultured with stimulator cells that are MHC incompatible, and certain donor combinations seem to work better than others.

Example 7

CLINICAL TRIALS

This example outlines the testing of implant compositions in conjunction with a peripherally administered cellular vaccine composition. The preparation and use of MLC tumor vaccines is described in more detail in International application WO 98/16238, which is hereby incorporated herein by reference in its entirety.

All patients are enrolled with informed consent, and randomized into the various treatment groups. Tumor cells are obtained during surgical resection of the primary neoplasm, and cryopreserve at the time of surgery. The tumor cells are proliferated ex vivo if necessary to obtain sufficient cells for the anticipated course of therapy. Thawed or cultured tumor cells are subjected to 10,000 rads of gamma irradiation. Preparative-scale mixed lymphocyte cultures using inactivated patient stimulator cells and donor leukocytes are conducted generally as described in Example 1.

The mononuclear cells used to prepare each cellular vaccine are obtained from healthy, unrelated donors. Donors are prescreened to minimize risk for infectious diseases as described in Example 7, and those that test positive are eliminated. By using genetically disparate donors, the likelihood of hyperacute rejection of the second administration is decreased. The mixed lymphocyte culture is conducted by mixing donor and inactivated patient peripheral blood mononuclear cells at a ratio of 10:1, and culturing at $3 \times 10^6$ cells/mL in AIMV supplemented with 2% fetal calf serum for 3 days at 37° C. The total number of mononuclear cells required for a single inoculum is no more than $1 \times 10^9$. The stimulated cells are collected and washed by centrifugation, then suspended in sterile, injectable saline. Quality control of the production of activated cells includes monitoring cell counts and viability, testing for mycoplasma and endotoxin, and monitoring for lymphocyte activation using early activation markers, as described in Example 7.

Before use in treatment, the alloactivated cell preparation is also evaluated according to functional release criteria. The Tetrazolium Reduction Assay (XTT described in Example 3 is conducted on a cell sample. Flow Cytometry is conducted to measure cell surface expression of CD69 using fluorescent antibody; or increased intracellular esterase activity using fluorescein diacetate. Cultured cells are considered to be sufficiently activated if the level measured in either one (but preferably both) of these assays is ≧10% above unstimulated donor control value on any day of the culture period (day 1, day 2, or day 3). Once the culture passes the criteria, testing on subsequent days is not needed. The cells are harvested on day 3, mixed with the requisite number of primary or cultured tumor cells, and prepared for human administration.

The study is conducted on patients with Stage IV (metastatic) colon cancer. Patents are enrolled in the study under terms of informed consent, and undergo a standard colectomy. About 1 week later (around the time they are discharged from the hospital), they begin a course of four vaccine injections.

The vaccine composition consists essentially of an alloactivated cell population mixed with tumor cells. Patients receive one of three different doses: $1 \times 10^8$ MLC cells; $3 \times 10^8$ MLC cells; or $1 \times 10^9$ MLC, mixed with up to $1 \times 10^7$ inactivated tumor cells, depending on availability. The same dose is given four times on a weekly schedule.

Initial studies are conducted primarily to determine the maximum tolerated dose (MTD). Undesirable clinical side effects at the injection site include an unacceptable level of induration, inflammation, or ulceration.

Once the MTD is determined, a comparison is made between the 4-week vaccination schedule alone, and a vaccination course initiated by direct implantation into a tumor mass. The implant group is treated two days to a week after colectomy, using ultrasound to guide an injection needle into a sizeable metastatic tumor mass in the liver. The metastatic site is injected with a preparation of $10 \times 10^9$ MLC alloactivated cells alone, suspended in a minimum volume of saline. Beginning one week later, the patients in this group also receive the 4-week course of the MLC-tumor cell vaccine.

Safety of the compositions is monitored by several criteria, including local induration, pruritus, or necrosis at the injection site; systemic effects such as fever, malaise, headache, and altered hematological or renal parameters.

The presence of a cellular immune response in the treated patient can be monitored by several criteria. Patient lymphocytes obtained before and after each inoculation are cultured with irradiated allogeneic cells of donor origin or from a third party (for anti-allotype response), or irradiated patient tumor cells, or third-party tumor cells (for specific anti-tumor response). The response of patient lymphocytes in culture is determined by measuring proliferation using reduction of MTT or one of the other functional assays as a surrogate marker for cellular division. Expression of CD69 is determined by immunofluorocytometry using PE-labeled antibody.

Optionally, the responding T cells are costained for CD4, CD8, or CD31 to identify helper or suppressor subsets, or for CD45RF to distinguish $T_{H1}$ from $T_{H2}$ cells. Cytokines IL-2, IL-4, IFN-γ and TNF-α secreted into the culture media are quantified by ELISA. IL-2 and IFN-γ correlate with $T_{H1}$ activity, IL-4 correlates with $T_{H2}$ activity, and TNF-αcorrelates with the activity of both. Patients' PBL are also optionally tested for their ability to respond to autologous tumor cells in culture. General T cell activation can be measured by the functional assays described in Example 3, [$^3$H] thymidine incorporation, or blastogenesis. Cytotoxic T cell activity can be measured as cytolysis of $^{51}$Cr labeled tumor cells. The effective delayed type hypersensitivity (DTH) anti-tumor response in the treated patient is measured by comparing the 48-hour response of the intradermal administration of $5 \times 10^5$ autologous tumor cells, mumps, tricophyton, or PPD antigens with that observed for the same series before treatment.

The patients are monitored for the extent of the clinical and immunological response for at least three months following therapy. Clinical criteria is monitored, in part, by tracking the volume of tumor metastasis present in the liver. A CT scan is performed at regular intervals, the volume of each metastatic site is calculated, and the volumes are compared with the measurements obtained before treatment. Progression of disease is indicated by an increase in volume of the metastasis, or an increase in the number of metastatic sites. A successful outcome is indicated by reversal of the disease, or slower progression in comparison with the typical outcome for patents with colon cancer of the same grade.

Example 8

COMMERCIAL PRODUCTION OF ALLOACTIVATED CELL COMPOSITIONS

This protocol describes the overall approach to production of the mixed lymphocyte culture. The design of this methodology takes into account Good Manufacturing (GMP) and Good Laboratory (GLP) Practices, and complies with requirements of Code 21 of U.S. Federal Regulations.

Patient peripheral blood mononuclear cells, at least $2 \times 10^9$ cells are collected by modified leukapheresis from the patient to be treated. Isolation of cells is performed on a Baxter Fenwall apheresis machine or equivalent machine using the Stem Cell Collection Procedure. Cells are shipped in a Baxter-type component bag on ice (4–10° C.). Transit temperature is monitored using MONITOR-MARK™ Time/Temperature Tags.

Donor peripheral blood mononuclear cells, at least $10 \times 10^9$ cells, are collected by modified leukapheresis from a healthy individual. Isolation of cells is performed on a Baxter Fenwall apheresis machine or equivalent, using the Stem Cell Collection Procedure. Donors are unrelated, anonymous, and random individuals, picked from a list of prescreened potential donors.

Prescreening of the donors should indicate negative risk factors for HIV, Hepatitis, Spongioform Encephalitides, or Tuberculosis. Each cell component is tested negative for HIV ½ Ab, HIV Ag, CMV Ab, HTLV I/II Ab, HCV Ab, HBcAb, HBsAg and RPR. Cells are shipped in a Baxter-type component bag on ice (4–10° C.).

Upon receipt each component is tested for sterility, appropriate cell counts, and viability. Components are maintained at 4–10° C. until use, and used or frozen within 72 hours of collection. Thawed frozen material are used within 2 hours and not re-frozen. Pre-clinical studies indicate that components stored at 4° C. in ACD anticoagulated plasma or material frozen in DMSO-containing media are suitable for the production of effective cell compositions.

Plasma is removed form both the donor and patient components by centrifugation. Donor plasma may be collected and heat-inactivated for use as a medium supplement. Component cells are suspended in small volumes of PBS and appropriate volumes of each suspension is mixed to produce a culture that contains $3 \times 10^6$ mononuclear cells/ml in AIMV medium at a ratio of 10:1 to 20:1 (donor:patient cells). Heat-inactivated donor plasma is added to a final concentration of 2%. Mixed cells are pumped into Fenwall 3 liter gas permeable culture bags through the use of the Fenwall solution pump and sterile set-up. Samples of the component cells may also be set up in small culture tubes for testing of lymphocyte activation. Testing of functional activity is compared with control cultures containing unstimulated donor cells alone.

Cell mixtures are cultured in a ISO-° 9000 Forma 37° C. incubator with 5% humidified and HEPA filtered $CO_2$ for 3 days, and closely monitored. Cells are harvested after culture by centrifugation. Samples are taken for quality assurance assays. Each preparation is tested for final sterility, adequate cell counts, adequate viability and functional activity.

The cell preparation is suspended in sterile 25% human albumin, and placed in sterile injectable vials for transport. Each preparation is labeled with an expiration date and time, which is 30 hours after packaging, and accompanied by appropriate instructions, release specification results, and a MONITOR-MARK™ Time/Temperature Tag. Cell preparations are packaged and shipped via overnight courier service. If not used immediately, the cells are stored in a refrigerator at 4–10° C. Any preparation not implanted before the expiration date is discarded.

In process tests that measure product consistency include:

pre-screen infectious disease tests;

in process and final product sterility tests;

final product mycoplasma and endotoxin;

in process and final product cell counts; in process and final product viability ($\geq 85\%$).

Cells must also meet satisfactory functional criteria. Preparations not meeting any of these criteria are not used for treating patients.

TABLE 2

Donor and Patient Screening
(At Time Of Leukapheresis Procedure)

| TEST | METHOD (AS PER HOSPITAL BLOOD BANK SOPS) | SPECIFICATION |
|---|---|---|
| Pre-screen for risk factors | HIV Hepatitis Spongioform encephalitis Tuberculosis | Report Only |
| Adventitious agent screening | HIV 1 and 2 Ab HIV Ag HBs-Ag HBc Ab* HCV Ab HTLV 1 and 2 Ab CMV Ab* RPR | All negative* |

*Patient may be positive for HBcAb or CMV Ab, and components are labeled as such.
If CMV negative donor components are not available, a CMV Ab positive donor component may be used, even for CMV negative patients.

TABLE 3

Pre-Process Testing Of Donor And Patient Mononuclear Cells
(At Time Of Receipt At Facility, Prior To Irradiation)

| TEST | SPECIFICATION |
|---|---|
| Sterility | Sterile |
| Cell Count | |
| Patient: | $\geq 2 \times 10^9$ cells |
| Donor: | $\geq 10 \times 10^9$ cells |

TABLE 4

In Process Testing Of Alloactivated Cells

| TEST | ASSAY | SPECIFICATION |
|---|---|---|
| Bioactivity of lymphocytes activation (Tests on days 1, 2, and/or 3 of culture) | Tetrazolium Reduction Assay (XTT) | $\geq 10\%$ above unstimulated donor control value on any day of test |
| | Flow Cytometry (cell surface expression of CD69 by fluorescent antibody; or increased intracellular esterase activity by fluorescein diacetate) | $\geq 10\%$ above unstimulated donor control value on any day of test |

TABLE 5

Final Product Testing

| TEST | SPECIFICATION |
|---|---|
| Sterility | Sterile |
| Cell Count | $9 \times 10^9$ cells ($\pm 10\%$) |
| Viability | $\geq 85\%$ viable cells |
| Mycoplasma | Negative (results not available until after the implantation) |
| Endotoxin | $\leq 350$ EU/total body |

Although the foregoing description includes details of some preferred embodiments to facilitate understanding, the skilled practitioner will readily appreciate that substitutions and modifications may be implemented without departing from the invention. Examples in the disclosure should not be construed as limiting the scope of the invention, which is delineated by the appended claims.

What is claimed as the invention is:

1. A method for preparing a pharmaceutical composition containing alloactivated human donor lymphocytes for treating a tumor in a human patient, comprising the steps of:
    a) coculturing the following cells ex vivo:
        lymphocytes from a first human donor allogeneic to the patient, and leukocytes from a second human donor allogeneic to both the first human donor and the patient, so as to alloactivate the lymphocytes; and
    b) harvesting the cocultured cells and preparing them for human administration at a time after initiation of the coculturing when the harvested cells, upon implantation in the bed of a solid tumor in the patient, are effective in treating the solid tumor or eliciting an anti-tumor immunological response in the patient.

2. The method according to claim 1, wherein the cocultured cells are harvested at a time when implantation of the cocultured cells elicits a response in the patient against the tumor.

3. The method according to claim 1, wherein the cocultured cells are harvested at a time when a single implantation of the cocultured cells in the bed of the solid tumor is effective in the treatment of the tumor.

4. The method according to claim 1, wherein the harvesting in step a) is performed at about the time that at least one of the following criteria is met:
    i) when the level of secretion of IFN-γ by the cultured cells is highest; or
    ii) at about 48 to 72 hours after initiation of the culture.

5. The method according to claim 1, wherein leukocytes from at least two different human donors allogeneic to both the first human donor and the patient are cocultured in step a).

6. The method according to claim 1, wherein the coculturing of step a) is conducted in a medium containing an H2 receptor antagonist.

7. The method according to claim 6, wherein the H2 receptor antagonist is cimetidine.

8. The method according to claim 7, wherein the cimetidine is present in the culture medium at a concentration between about 5 μg/mL and about 100 μg/mL.

9. A method for preparing a cultured cell population containing alloactivated human donor lymphocytes effective in treating a tumor in a human patient, comprising the steps of:
    a) obtaining lymphocytes from a first human donor allogeneic to the patient, and
    b) obtaining leukocytes from a second human donor allogeneic to both the first human donor and the patient;
    c) coculturing the lymphocytes ex vivo with the leukocytes so as to alloactivate the lymphocytes;
    d) harvesting the cocultured cells from culture at a time when the harvested cells, upon implantation in the bed of a solid tumor in the patient, are effective in treating the tumor or eliciting an anti-tumor immunological response;
    e) washing culture medium from the harvested cells; and
    f) verifying that the washed cells are sufficiently sterile for human administration.

10. The method according to claim 9, incorporating one or more of the following features:
    i) obtaining at least about $2 \times 10^9$ peripheral blood mononuclear cells from the first human donor in step a);
    ii) obtaining at least about $2 \times 10^8$ peripheral blood mononuclear cells from the second human donor in step b);
    iii) blocking proliferation of the leukocytes prior to step c);
    iv) coculturing the donor lymphocytes with the patient leukocytes at a ratio of about 5:1 to 20:1 in step c); or
    v) producing at least about $2 \times 10^9$ cocultured cells suitable for human administration after completion of step f).

11. A pharmaceutical composition prepared according to the method of claim 1, which, upon implantation at or around the site of a solid tumor in said human patient with or without partial resection of the tumor, is effective in eliciting an anti-tumor immunological response.

12. A pharmaceutical composition prepared according to the method of claim 1, which, upon implantation at or around the site of a solid tumor in a human patient with or without partial resection of the tumor, is effective in the treatment of the tumor.

13. The pharmaceutical composition of claim 11 having one or more of the following features:
    i) containing between about $2 \times 10^9$ and $2 \times 10^{10}$ cultured peripheral blood mononuclear cells originating from the first donor;
    ii) containing between about $1 \times 10^8$ and $2 \times 10^9$ cultured peripheral blood mononuclear cells originating from the second donor;
    iii) being substantially free of any exogenously added lymphocyte proliferation agent;
    iv) containing a physiologically compatible carrier selected from the group consisting of physiological saline, buffered medium, and clotted plasma.

14. The pharmaceutical composition of claim 11, wherein a single implantation of the cocultured cells is effective in eliciting an anti-tumor immunological response.

15. A method of eliciting an anti-tumor immunological response in a human patient, comprising implanting in or around the bed of a solid tumor in the patient a pharmaceutical composition according to claim 10.

16. A method of treating a tumor in a human patient, comprising implanting in or around the bed of a solid tumor in the patient a pharmaceutical composition according to claim 12.

17. The method according to claim 14, further comprising the additional step of administering to the patient at a site distant from the tumor a second composition comprising alloactivated human lymphocytes allogeneic to the patient mixed with inactivated tumor cells from the patient or inactivated progeny of such tumor cells.

18. The method according to claim 15, wherein the tumor is a malignancy selected from the group consisting of melanoma, pancreatic cancer, liver cancer, colon cancer, prostate cancer, and breast cancer.

* * * * *

UNITED STATES PATENT AND TRADEMARK OFFICE
CERTIFICATE OF CORRECTION

PATENT NO. : 6,203,787 B1
DATED : March 20, 2001
INVENTOR(S) : Thompson et al.

It is certified that error appears in the above-identified patent and that said Letters Patent is hereby corrected as shown below:

Claim 15, column 38,
Line 46, please delete "10" and replace with -- 11 --;

Claim 17, column 38,
Line 51, please delete "14" and replace with -- 15 --.

Signed and Sealed this

Eleventh Day of September, 2001

*Attest:*

Nicholas P. Godici

NICHOLAS P. GODICI
*Attesting Officer*    *Acting Director of the United States Patent and Trademark Office*